(12) United States Patent
Ono

(10) Patent No.: US 10,842,375 B2
(45) Date of Patent: Nov. 24, 2020

(54) OPHTHALMOLOGIC APPARATUS AND METHOD OF CONTROLLING THE SAME

(71) Applicant: TOPCON CORPORATION, Tokyo (JP)

(72) Inventor: Yusuke Ono, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 157 days.

(21) Appl. No.: 16/112,803

(22) Filed: Aug. 27, 2018

(65) Prior Publication Data

US 2019/0059721 A1    Feb. 28, 2019

(30) Foreign Application Priority Data

Aug. 28, 2017 (JP) ................. 2017-163506

(51) Int. Cl.
*A61B 3/14* (2006.01)
*A61B 3/00* (2006.01)
(Continued)

(52) U.S. Cl.
CPC .............. *A61B 3/14* (2013.01); *A61B 3/0025* (2013.01); *A61B 3/102* (2013.01); *A61B 3/113* (2013.01);
(Continued)

(58) Field of Classification Search
CPC .. A61B 3/15; A61B 3/152; A61B 3/14; A61B 3/0025; A61B 3/102; A61B 3/113; A61B 3/145
(Continued)

(56) References Cited

U.S. PATENT DOCUMENTS 9,011,418 B2* 4/2015 Campin ................. A61B 3/152
606/4
2014/0211157 A1 7/2014 Nakahara et al.
(Continued)

FOREIGN PATENT DOCUMENTS

EP 2859838 A1 4/2015
EP 3040017 A1 7/2016
(Continued)

OTHER PUBLICATIONS

Extended European Search Report dated Feb. 20, 2019 in European Application No. 18188255.6-1124.

*Primary Examiner* — Zachary W Wilkes
(74) *Attorney, Agent, or Firm* — Xsensus LLP

(57) ABSTRACT

An ophthalmologic apparatus includes an image sensor that acquires first and second images of an anterior segment of a subject's eye at different timings, and processing circuitry that calculates a rotational movement amount between a partial image in the second image and a corresponding partial image in the first image. The processing circuitry performs registration between the partial images in a rotation direction based on the rotational movement amount and performs a phase only correlation processing to calculate a parallel movement amount. The processing circuitry controls an actuator that moves the subject's eye and the optical system relative to each other based on at least one of the rotational movement amount and the parallel movement amount, specifies the partial image in the second image based on the first image and the second image, and calculates the rotational movement amount between the corresponding partial image and the specified partial image.

6 Claims, 12 Drawing Sheets

(51) Int. Cl.

| | |
|---|---|
| *A61B 3/10* | (2006.01) |
| *A61B 3/113* | (2006.01) |
| *A61B 3/15* | (2006.01) |
| *A61B 3/12* | (2006.01) |
| *G06T 7/246* | (2017.01) |
| *G06T 7/32* | (2017.01) |
| *G06T 7/33* | (2017.01) |
| *G06T 7/262* | (2017.01) |
| *A61B 3/117* | (2006.01) |
| *A61B 90/00* | (2016.01) |

(52) U.S. Cl.
CPC ............... *A61B 3/12* (2013.01); *A61B 3/145* (2013.01); *A61B 3/152* (2013.01); *G06T 7/248* (2017.01); *G06T 7/262* (2017.01); *G06T 7/32* (2017.01); *G06T 7/337* (2017.01); *A61B 3/0041* (2013.01); *A61B 3/0075* (2013.01); *A61B 3/117* (2013.01); *A61B 2090/364* (2016.02); *G06T 2207/10101* (2013.01); *G06T 2207/20021* (2013.01); *G06T 2207/30041* (2013.01)

(58) Field of Classification Search
USPC ........................................ 351/206, 209, 246
See application file for complete search history.

(56) References Cited

U.S. PATENT DOCUMENTS

| | | | |
|---|---|---|---|
| 2015/0138502 | A1 | 5/2015 | Moriguchi et al. |
| 2016/0198940 | A1* | 7/2016 | Shibutani ........... G06K 9/00604 351/206 |

FOREIGN PATENT DOCUMENTS

| | | |
|---|---|---|
| JP | 2015-43898 A | 3/2015 |
| JP | 2018-075444 A | 5/2018 |

\* cited by examiner

OPHTHALMOLOGIC APPARATUS AND METHOD OF CONTROLLING THE SAME

CROSS-REFERENCE TO RELATED APPLICATION

This application is based upon and claims the benefit of priority from Japanese Patent Application No. 2017-163506, filed Aug. 28, 2017; the entire contents of which are incorporated herein by reference.

FIELD

Embodiments according to present invention described herein relate to an ophthalmologic apparatus and a method of controlling the same.

BACKGROUND

Examples of the ophthalmologic apparatus for photographing a subject's eye include an optical coherence tomography (OCT) apparatus using OCT, a fundus camera, a scanning laser ophthalmoscope (SLO), a slit lamp, and the like. Among them, OCT has been drawing attention. OCT creates an image representing the exterior structure, interior structure, or the like of a target eye using light beams from a laser light source or the like. Unlike X-ray computed tomography (CT), OCT is not invasive on the human body, and therefore is expected to be applied to the medical field and the biological field, in particular. For example, in the field of ophthalmology, apparatuses have been put to practical use for forming images of an anterior segment, etc. of the subject's eye or measuring the intraocular distance.

For the ophthalmologic apparatus like this, tracking is an important technique to obtain a high-definition image or to measure with high accuracy regardless of the eye movement of the subject's eye. Tracking is an operation to move the optical system of the apparatus according to eye movements of the subject's eye. To perform tracking, alignment and focusing are performed in advance. In other words, tracking is a function of maintaining a suitable positional relationship in which alignment and focusing are matched by causing the position of an optical system of the apparatus and the like to follow the eye movement. Various types of methods relating to such tracking are suggested.

For example, Japanese Unexamined Patent Application Publication No. 2015-043898 discloses an ophthalmologic apparatus that acquires a base image of a fundus and a target image of the fundus using a fundus camera, performs a phase only correlation processing on the base image and the target image to obtain a minute misregistration amount, and performs tracking based on the obtained misregistration amount.

SUMMARY

The first aspect of the embodiments is an ophthalmologic apparatus comprising: an optical system for acquiring data of a subject's eye optically; an image acquiring unit that acquires a first image of an anterior segment of the subject's eye and a second image of the anterior segment at different timings from each other; a rotational movement amount calculator that calculates a rotational movement amount between a partial image in the second image and a corresponding partial image in the first image, the corresponding partial image corresponding to the partial image; a registration unit that performs registration between the corresponding partial image and the partial image in a rotation direction based on the rotational movement amount; a parallel movement amount calculator that performs a phase only correlation processing on the corresponding partial image and the partial image registered by the registration unit to calculate a parallel movement amount between the corresponding partial image and the partial image; a movement mechanism that moves the subject's eye and the optical system relative to each other; and a controller that controls the movement mechanism based on at least one of the rotational movement amount and the parallel movement amount.

Further, the second aspect of the embodiments is the ophthalmologic apparatus, in the first aspect, further comprising: a specifying unit that specifies the partial image in the second image, wherein the rotational movement calculator may calculate the rotational movement amount between the corresponding partial image and the partial image specified by the specifying unit.

Further, the third aspect of the embodiments is the ophthalmologic apparatus, in the second aspect, wherein the specifying unit may specify the partial image based on the first image and the second image.

Further, the fourth aspect of the embodiments is the ophthalmologic apparatus, in the third aspect, wherein the specifying unit may specify, as the partial image, an image of a region of which movement amount with respect the first image is equal to or larger than a first threshold value in the second image.

Further, the fifth aspect of the embodiments is the ophthalmologic apparatus, in the third aspect, wherein the specifying unit may specify a region of which movement amount with respect the first image is equal to or less than a second threshold value in the second image, and may specify, as the partial image, an image of a region other than the specified region in the second image.

Further, the sixth aspect of the embodiments is the ophthalmologic apparatus, in the second aspect, wherein the specifying unit may specify an image of a region in which an eyelid or an eyelash is represented in the second image, and may specify, as the partial image, an image of a region other than the specified region in the second image.

Further, the seventh aspect of the embodiments is the ophthalmologic apparatus, in the second aspect, wherein the specifying unit may specify, as the partial image, an image of a predetermined region in the second image.

Further, the eighth aspect of the embodiments is the ophthalmologic apparatus, in the seventh aspect, wherein the predetermined region may include a region corresponding to a pupil of the subject's eye, and may be a region where upper eyelid, lower eyelid, and an eyelash of the subject's eye are not represented.

Further, the ninth aspect of the embodiments is the ophthalmologic apparatus, in any one of the first to the eighth aspects, wherein the rotational movement amount calculator may perform the phase only correlation processing on the corresponding partial image and the partial image to calculate the rotational movement amount.

Further, the tenth aspect of the embodiments is a method of controlling an ophthalmologic apparatus comprising: an optical system for acquiring data of a subject's eye optically; an image acquiring unit that acquires a first image of an anterior segment of the subject's eye and a second image of the anterior segment at different timings from each other; and a movement mechanism that moves the subject's eye and the optical system relative to each other, the method comprising: a rotational movement amount calculating step of calculating a rotational movement amount between a partial image in the second image and a corresponding partial image in the first image, the corresponding partial image corresponding to the partial image; a registration step of performing registration between the corresponding partial image and the partial image in a rotation direction based on the rotational movement amount; a parallel movement amount calculating step of performing a phase only correlation processing on the corresponding partial image and the partial image registered in the registration step to calculate a parallel movement amount between the corresponding partial image and the partial image; and a control step of controlling the movement mechanism based on at least one of the rotational movement amount and the parallel movement amount.

Further, the eleventh aspect of the embodiments is the method of controlling the ophthalmologic apparatus, in the tenth aspect, further comprising: a specifying step of specifying the partial image in the second image, wherein the rotational movement amount calculating step may comprise calculating the rotational movement amount between the corresponding partial image and the partial image specified in the specifying step.

Further, the twelfth aspect of the embodiments is the method of controlling the ophthalmologic apparatus, in the eleventh aspect, wherein the specifying step may comprise specifying an image of a region of which movement amount with respect the first image is equal to or larger than a first threshold value in the second image, as the partial image.

Further, the thirteenth aspect of the embodiments is the method of controlling the ophthalmologic apparatus, in the eleventh aspect, wherein the specifying step may comprise specifying a region of which movement amount with respect the first image is equal to or less than a second threshold value in the second image, and specifying an image of a region other than the specified region in the second image as the partial image.

Further, the fourteenth aspect of the embodiments is the method of controlling the ophthalmologic apparatus, in the eleventh aspect, wherein the specifying step may comprise specifying a predetermined region in the second image as the partial image.

The various features of the above aspects may be variously combined with some features included and others excluded to suit a variety of different applications.

DETAILED DESCRIPTION

Figure 1:
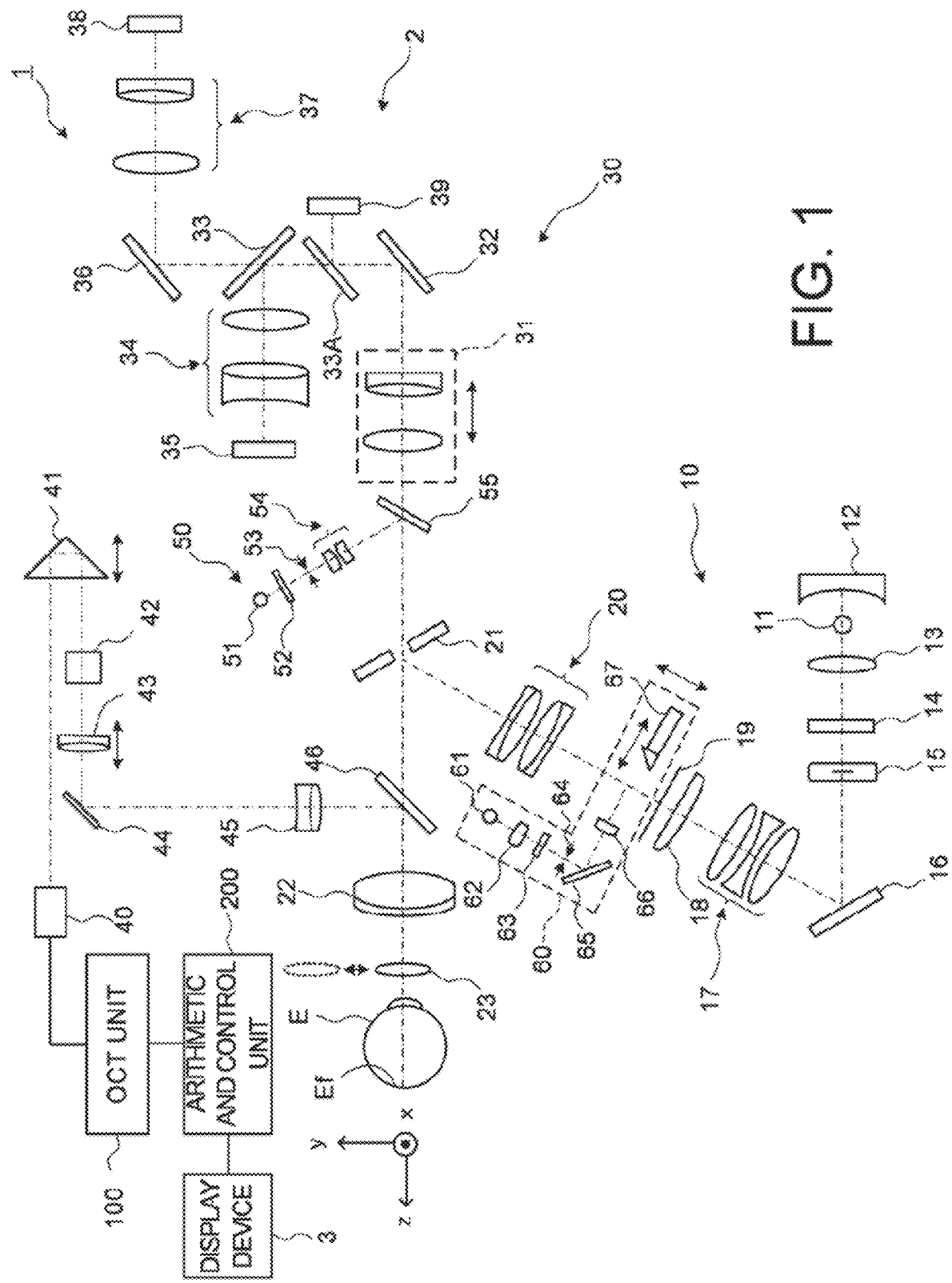
FIG. 1 is a schematic diagram illustrating an example of the configuration of an optical system of an ophthalmologic apparatus according to embodiments.

When measuring or photographing of an anterior segment of a subject's eye is performed, an anterior segment image is acquired and control of tracking is performed by using the anterior segment image. However, eyelids, eyelashes, or the like that don't move are depicted in the anterior segment image besides a pupil area moving by the eye movement. Thus, misregistration amount cannot be obtained by using a phase only correlation processing.

According to some embodiments of the present invention, a technique for performing tracking with high precision in case of measuring or imaging an anterior segment of a subject's eye can be provided.

Referring now to the drawings, exemplary embodiments of an ophthalmologic apparatus and a method of controlling the same according to the present invention are described below. Any of the contents of the documents cited in the present specification and arbitrary known techniques may be applied to the embodiments below.

An ophthalmologic apparatus according to the embodiments has at least a function of performing OCT. The ophthalmologic apparatus is a measurement apparatus capable of acquiring information on an object to be measured by performing OCT on the object to be measured. Hereinafter, a case will be described where the ophthalmologic apparatus according to the embodiments is an ophthalmologic apparatus that images of a living eye by performing OCT on the living eye that is an object to be measured. However, embodiments are not limited thereto. For example, the ophthalmologic apparatus according to the embodiments may be capable of measuring the intraocular distance of a living eye such as the axial length by performing OCT on the living eye.

The ophthalmologic apparatus according to the embodiments is an ophthalmologic apparatus that is a combination of a Fourier domain OCT apparatus and a fundus camera. The ophthalmologic apparatus has a function of performing swept source OCT, but the embodiments are not limited to this. For example, the type of OCT is not limited to swept source OCT, and it may be the spectral domain OCT or the like. The swept source OCT is a technique that splits light from a wavelength tunable type (i.e., a wavelength scanning type) light source into measurement light and reference light; superposes the measurement light returning from the object to be measured with the reference light to generate interference light; detects the interference light with a balanced photodiode or the like; and applies the Fourier transform etc. to the detection data acquired through the tuning of wavelengths and the scanning of the measurement light to form an image. The spectral domain OCT is a technique that splits light from a low coherence light source into measurement light and reference light; superposes the measurement light returning from the object to be measured with the reference light to generate interference light; detects the spectral distribution of the interference light with a spectrometer; and applies the Fourier transform etc. to the detected spectral distribution to form an image.

The ophthalmologic apparatus according to the embodiments may include a scanning laser ophthalmoscope (SLO), a slit lamp microscope, an anterior segment photographing camera, a surgical microscope, a photocoagulator, etc. in place of or in addition to the fundus camera. In the present specification, a measuring by OCT is referred to as a "OCT measurement" and an image acquired using OCT is referred to as an OCT image. The optical path of the measurement light is denoted as a "measurement optical path", and the optical path of the reference light is denoted as a "reference optical path".

[Configuration]

As shown in FIG. 1, the ophthalmologic apparatus according to the embodiments includes a fundus camera unit 2, an OCT unit 100, and an arithmetic and control unit 200. The fundus camera unit 2 has substantially the same optical system as the conventional fundus camera. The OCT unit 100 is provided with an optical system for performing OCT. The arithmetic and control unit 200 is provided with one or more processors for performing various kinds of arithmetic processing, control processing, and the like.

In the present specification, the term "processor" is used to mean, for example, a circuity including a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the function according to the embodiments, for example, by read out a computer program stored in a storage circuit or a storage device and executing the computer program.

[Fundus Camera Unit]

The fundus camera unit 2 is provided with an optical system for acquiring two dimensional images (fundus images) rendering the surface morphology of the fundus Ef of the subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. In addition, the fundus camera unit 2 is provided with an illumination optical system 10 and an imaging optical system 30. The illumination optical system 10 projects illumination light onto the fundus Ef The imaging optical system 30 guides the illumination light reflected from the fundus Ef to imaging devices (CCD image sensors 35 and 38). Each of the CCD image sensors 35 and 38 is sometimes simply referred to as a "CCD". Further, the imaging optical system 30 guides measurement light coming from the OCT unit 100 to the subject's eye E, and guides the measurement light returning from the subject's eye E to the OCT unit 100.

The observation light source 11 of the illumination optical system 10 includes, for example, a halogen lamp or a light emitting diode (LED). The light (observation illumination light) output from the observation light source 11 is reflected by a reflective mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding area of an aperture part) of an aperture mirror 21, penetrates a dichroic mirror 46, and refracted by an objective lens 22, thereby illuminating the fundus Ef.

The observation illumination light reflected from the fundus Ef is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the fundus reflection light passes through a half mirror 33A, is reflected by a dichroic mirror 33, and forms an image on the light receiving surface of the CCD image sensor 35 by a condenser lens 34. The CCD image sensor 35 detects the fundus reflection light at a predetermined frame rate, for example. An image (observation image) based on the fundus reflection light detected by the CCD image sensor 35 is displayed on a display device 3. Note that when the imaging optical system 30 is focused on the anterior segment, reflection light of the observation illumination light from the anterior segment is detected by the CCD image sensor 35 and an observation image of the anterior segment based on the reflection light is displayed on the display device 3.

The imaging light source 15 is formed of, for example, a xenon lamp or an LED. The light (imaging illumination light) output from the imaging light source 15 is projected onto the fundus Ef via the same route as that of the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source. Note that when the imaging optical system 30 is focused on the anterior segment, reflection light of the observation illumination light from the anterior segment is detected by the CCD image sensor 38 and an observation image (photographed image) of the anterior segment based on the reflection light is displayed on the display device 3.

A liquid crystal display (LCD) 39 displays a fixation target and a visual target used for visual acuity measurement. The fixation target is a visual target for fixating the subject's eye E, and is used when performing fundus photography and OCT measurement, and the like.

Part of the light output from the LCD 39 is reflected by the half mirror 33A, is reflected by the mirror 32, travels through the photography focusing lens 31 and the dichroic mirror 55, and passes through the aperture part of the aperture mirror 21. The light having passed through the aperture part of the aperture mirror 21 penetrates the dichroic mirror 46, and is refracted by the objective lens 22, thereby being projected onto the fundus Ef. By changing the display position of the fixation target on the screen of the LCD 39, the fixation position of the subject's eye E can be changed.

Further, as with conventional fundus cameras, the fundus camera unit 2 is provided with an alignment optical system 50 and a focus optical system 60. The alignment optical system 50 generates an indicator (referred to as an alignment indicator) for the position adjustment (i.e., the alignment) of the optical system with respect to the subject's eye E. The focus optical system 60 generates an indicator (referred to as a split indicator) for adjusting the focus with respect to the subject's eye E.

The light output from an LED 51 of the alignment optical system 50 (i.e., alignment light) travels through the diaphragms 52 and 53 and the relay lens 54, is reflected by the dichroic mirror 55, and passes through the aperture part of the aperture mirror 21. The alignment light having passed through the aperture part of the aperture mirror 21 penetrates the dichroic mirror 46, and is projected onto the cornea of the subject's eye E by the objective lens 22.

The alignment light reflected from the cornea travels through the objective lens 22, the dichroic mirror 46 and the above-mentioned aperture part. Part of the cornea reflection light penetrates the dichroic mirror 55 and passes through the photography focusing lens 31. The cornea reflection light having passed through the photography focusing lens 31 is reflected by the mirror 32, penetrates the half mirror 33A, is reflected by the dichroic mirror 33, and is projected onto the light receiving surface of the CCD image sensor 35 by the condenser lens 34. The received image (i.e., alignment indicator image) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

The focus optical system 60 is movable along an optical path of the illumination optical system 10. The photography focusing lens 31 is movable along an optical path of the imaging optical system 30 in conjunction with the movement of the focus optical system 60. The reflection rod 67 of the focus optical system 60 can be inserted and removed into and from the illumination optical path.

To conduct focus adjustment, the reflective surface of the reflection rod 67 is arranged in a slanted position on the illumination optical path. The light output from the LED 61 of the focus optical system 60 (i.e., focus light) passes through the relay lens 62, is split into two light fluxes by the split indicator plate 63, passes through the two-hole diaphragm 64. The light having passed through the two-hole diaphragm 64 is reflected by the mirror 65, is converged on the reflective surface of the reflection rod 67 by the condenser lens 66, and is reflected by the reflective surface. The light reflected by the reflective surface of the reflection rod 67 travels through the relay lens 20, is reflected by the aperture mirror 21, penetrates the dichroic mirror 46, and is refracted by the objective lens 22, thereby being projected onto the fundus Ef as a pair of split indicator light(s).

The pair of split indicator light passing through a pupil of the subject's eye E reach the fundus Ef of the subject's eye E. The fundus reflection light of the pair of split indicator light passes through the pupil and passes through the same route as the fundus reflection light flux of the illumination light and is detected by the CCD image sensor 35. The received image (i.e., a pair of split indicator images) captured by the CCD image sensor 35 is displayed on the display device 3 together with the observation image. As in the conventional case, the arithmetic and control unit 200 can analyze positions of the pair of split indicator images, and move the focus optical system 60 for the focus adjustment (automatic focusing). A fundus image is formed on the imaging surface of the CCD image sensor 35 by moving the photography focusing lens 31 in conjunction with the movement of the focus optical system 60. Instead, the user may manually perform the focus adjustment while visually checking the pair of split indicator images (by operating the operation unit 240B described later).

The reflection rod 67 is inserted at a position on the illumination optical path substantially optically conjugate with the fundus Ef of the subject's eye E. The position of the reflective surface of the reflection rod 67 inserted in the optical path of the illumination optical system 10 is a position substantially optically conjugate with the split indicator plate 63. As described above, the split indicator light is split into two fluxes by the action of the two-hole diaphragm 64 and the like. When the fundus Ef and the reflective surface of the reflection rod 67 are not optically conjugate with each other, the pair of split indicator images acquired by the CCD image sensor 35 are displayed on the display device 3 in such a way that the split indicator images are separated in the right-and-left direction, for example When the fundus Ef and the reflective surface of the reflection rod 67 are substantially optically conjugate with each other, the pair of split indicator images are displayed on the display device 3 in such a way that the positions of the split indicator images acquired by the CCD image sensor 35 coincide with each other in the vertical direction, for example. When the focus optical system 60 is moved along the illumination optical path so that the fundus Ef and the split indicator plate 63 are always optically conjugate with each other, the photography focusing lens 31 is moved along the imaging optical path in conjunction with the movement of the focus optical system 60. When the fundus Ef and the split indicator plate 63 are not optically conjugate with each other, the pair of split indicator images are separated into two. Thus, the position of the photography focusing lens 31 is obtained by moving the focus optical system 60 so that the pair of split indicator images coincide with each other in the vertical direction. In the present embodiment, the case where the pair of split indicator images are acquired has been described, but the number of split indicator images may be three or more.

The dichroic mirror 46 branches an optical path for OCT from an optical path for observing and imaging of the fundus. The dichroic mirror 46 reflects light of wavelengths used for OCT, and transmits light for observing and imaging of the fundus. The optical path for OCT is provided with, in order from the OCT unit 100 side, a collimator lens unit 40, an optical path length changing unit 41, an optical scanner 42, an OCT focusing lens 43, a mirror 44, and a relay lens 45.

The collimator lens unit 40 includes a collimator lens. The collimator lens unit 40 is optically connected to the OCT unit 100 with an optical fiber. The collimator lens in the collimator lens unit 40 is disposed at a position facing the emitting end of the optical fiber. The collimator lens unit 40 converts the measurement light LS (described later) emitted from the emitting end of the optical fiber into a parallel light flux and converges the returning light of the measurement light LS from the subject's eye E to the emitting end of the optical fiber.

The optical path length changing unit 41 is movable in directions indicated by the arrow in FIG. 1, thereby changing the length of the optical path for OCT measurement. This change in the optical path length is used for correcting the optical path length according to the axial length of the subject's eye E, adjusting the interference state, and the like. The optical path length changing unit 41 includes, for example, a corner cube and a mechanism for moving the corner cube.

The optical scanner 42 is disposed at a position optically conjugate with the pupil of the subject's eye E, for example. The optical scanner 42 changes the traveling direction of the light (measurement light LS) passing through the OCT optical path. Thereby, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano minors. Thereby, it is possible to scan with the measurement light LS in an arbitrary direction in the xy plane.

The OCT focusing lens 43 is movable along the optical path of the measurement light LS (an optical axis of an interference optical system).

The ophthalmologic apparatus 1 is provided with a front lens 23 capable of being arranged between the subject's eye E and the objective lens 22. The front lens 23 can be manually arranged between the subject's eye E and the objective lens 22. The front lens 23 may be capable to be arranged between the subject's eye E and the objective lens 22 under the control of a controller 210 described later. In the case that the front lens 23 is removed from between the subject's eye E and the objective lens 22, a focal position of the measurement light is located at the fundus Ef of the subject's eye E or in vicinity of the fundus Ef. Thereby, OCT measurement of the fundus Ef can be performed. In the case that the front lens 23 is arranged between the subject's eye E and the objective lens 22, a focal position of the measurement light is moved to the anterior segment or in vicinity of the anterior segment. Thereby, OCT measurement of the anterior segment can be performed.

[OCT Unit]

Figure 2:
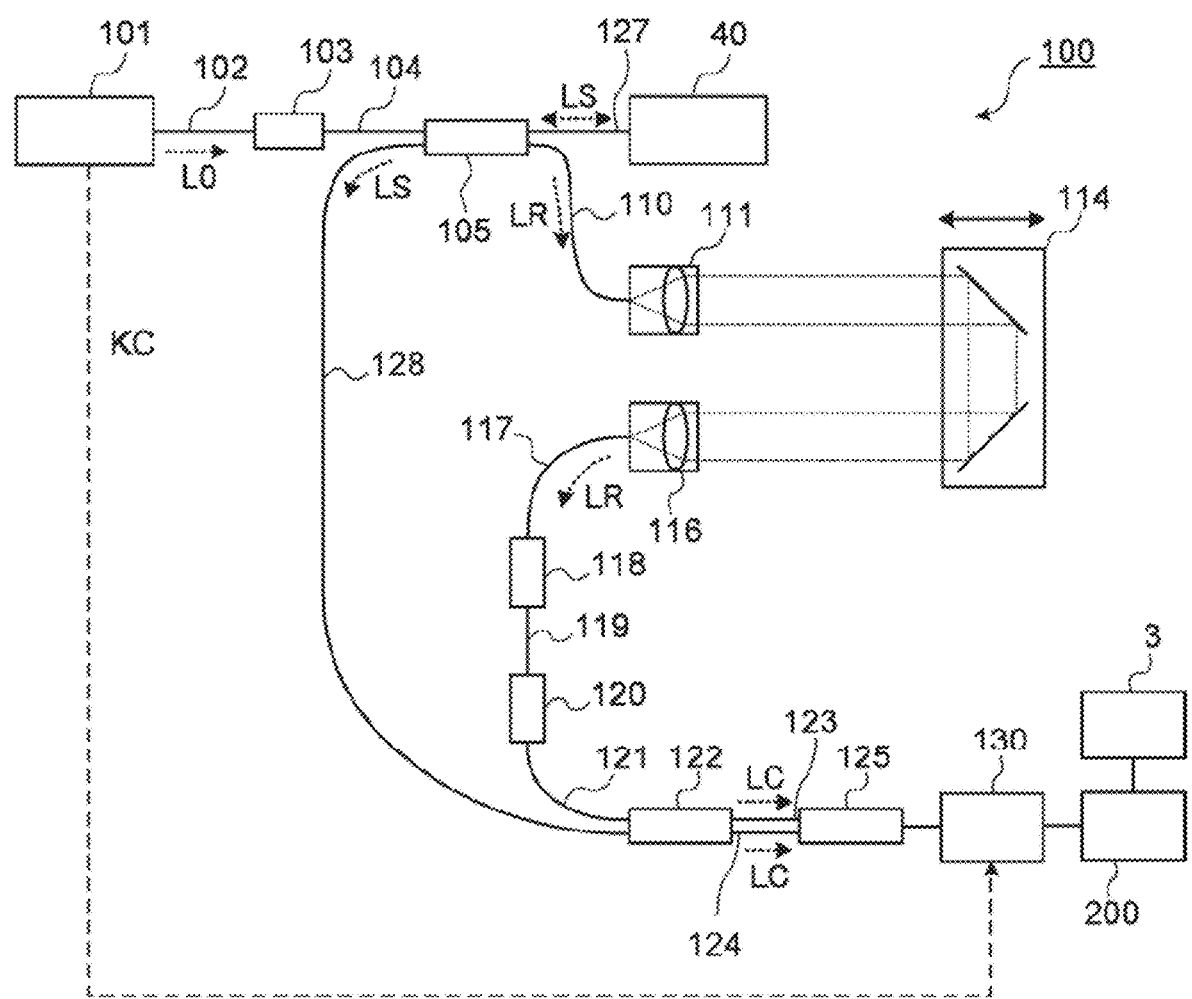
FIG. 2 is a schematic diagram illustrating an example of the configuration of an optical system of the ophthalmologic apparatus according to the embodiments.

Exemplary configuration of the OCT unit 100 is shown in FIG. 2. The OCT unit 100 includes an optical system for acquiring OCT images of the subject's eye E. This optical system is an interference optical system that splits light from the wavelength tunable type (wavelength scanning type) light source into the measurement light and a reference light, make the measurement light returning from the subject's eye E and the reference light having traveled through a reference optical path interfere with each other to generate interference light, and to detect the interference light. The detection result of the interference light obtained by the interference optical system (i.e., the detection signal) is an interference signal indicating the spectrum of the interference light, and is sent to the arithmetic and control unit 200.

Like swept source type ophthalmologic apparatuses commonly used, the light source unit 101 includes a wavelength tunable type (i.e., a wavelength scanning type) light source capable of sweeping (scanning) the wavelengths of emitted light. The wavelength tunable type light source includes a laser light source that includes a resonator. The light source unit 101 temporally changes the output wavelengths within the near infrared wavelength bands that cannot be visually recognized with human eyes.

Light L0 output from the light source unit 101 is guided to a polarization controller 103 through an optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to a fiber coupler 105 through an optical fiber 104 and is split into the measurement light LS and the reference light LR.

The reference light LR is guided to a collimator 111 through an optical fiber 110 and becomes a parallel light flux. The reference light LR, which has become a parallel light flux, is guided to the optical path length changing unit 114. The optical path length changing unit 114 is movable in directions indicated by the arrow in FIG. 2, thereby changing the length of the optical path of the reference light LR. Through this movement, the length of the optical path of the reference light LR is changed. This change in the optical path length is used for correcting the optical path length according to the axial length of the subject's eye F, adjusting the interference state, and the like. The optical path length changing unit 114 includes, for example, a corner cube and a mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The configuration shown in FIG. 1 and FIG. 2 includes both the optical path length changing unit 41 that changes the length of the optical path of the measurement light LS (i.e., measurement optical path or measurement arm) and the optical path length changing unit 114 that changes the length of the optical path of the reference light LR (i.e., reference optical path or reference arm). However, any one of the optical path length changing units 41 and 114 may be provided. The difference between the measurement optical path length and the reference optical path length can be changed by using other optical members.

The reference light LR that has traveled through the optical path length changing unit 114 is converted from the parallel light flux to the convergent light flux by the collimator 116 and enters the optical fiber 117.

An optical path length correction member may be disposed in at least one of the reference optical path between the collimator 111 and the optical path length changing unit 114 and the reference optical path between the collimator 116 and the optical path length changing unit 114. The optical path length correction member functions as a delaying means for matching the optical path length (i.e., optical distance) of the reference light LR with the optical path length of the measurement light LS.

The reference light LR that has entered the optical fiber 117 is guided to the polarization controller 118. With the polarization controller 118, the polarization state of the reference light LR is adjusted. The polarization controller 118 has the same configuration as, for example, the polarization controller 103. The reference light LR whose polarization state has been adjusted by the polarization controller 118 is guided to an attenuator 120 through an optical fiber 119 and the light amount is adjusted under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided to the collimator lens unit 40 through an optical fiber 127, and is made into a parallel light flux by the collimator lens unit 40. The measurement light LS made into the parallel light flux is guided to the dichroic mirror 46 via the optical path length changing unit 41, the optical scanner 42, the OCT focusing lens 43, the mirror 44, and the relay lens 45. The measurement light LS guided to the dichroic mirror 46 is reflected by the dichroic mirror 46, is refracted by the objective lens 22, and is projected onto the subject's eye E. The measurement light LS is scattered (and reflected) at various depth positions of the subject's eye E. Returning light of the measurement light LS including such backscattered light advances through the same path as the outward path in the opposite direction and is guided to the fiber coupler 105, and then reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light(s) LC by splitting the interference light generated from the measurement light LS and the reference light LR at a predetermined splitting ratio (for example, 1:1). The pair of interference light LC emitted from the fiber coupler 122 are guided to a detector 125 through optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the data acquisition system (DAQ) 130. The clock KC is supplied from the light source unit 101 to the DAQ 130. The clock KC is generated in the light source unit 101 in synchronization with the output timing of each wavelength sweeping (i.e., wavelength scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic and control unit 200 forms image data by applying imaging processing to the reflection intensity profiles of the respective A lines.

[Arithmetic and Control Unit]

The configuration of the arithmetic and control unit 200 will be described. The arithmetic and control unit 200 analyzes the interference signals input from the detector 125 to form an OCT image of the subject's eye E. The arithmetic processing for the OCT image formation is performed in the same manner as in the conventional swept source type ophthalmologic apparatus.

Further, the arithmetic and control unit 200 controls the fundus camera unit 2, the display device 3, and the OCT unit 100. For example, the arithmetic and control unit 200 controls the display device 3 to display the OCT image of the subject's eye E.

Like conventional computers, the arithmetic and control unit 200 includes a microprocessor, a random access memory (RAM), a read only memory (ROM), a hard disk drive, a communication interface, and the like. The storage device such as a hard disk drive stores computer programs for controlling the ophthalmologic apparatus 1. The arithmetic and control unit 200 may include various kinds of circuitry such as a circuit board for forming OCT images, for example. In addition, the arithmetic and control unit 200 may include an operation device (input device) such as a keyboard and a mouse, and a display device such as an LCD.

[Control System]

Figure 3:
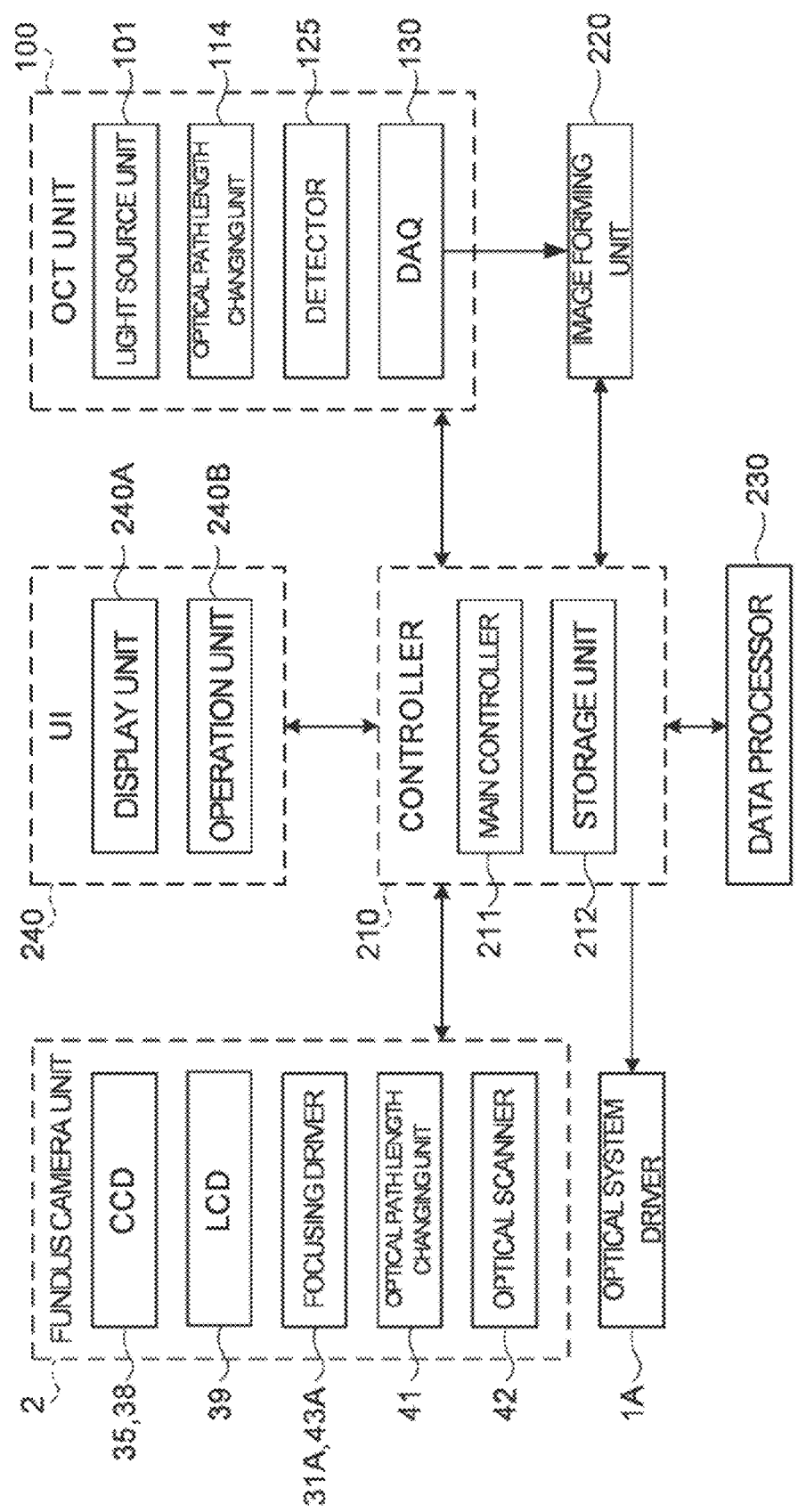
FIG. 3 is a schematic diagram illustrating an example of the configuration of a processing system of the ophthalmologic apparatus according to the embodiments.

The configuration of the control system of the ophthalmologic apparatus 1 will be described with reference to FIGS. 3, 4, 6, and 7. In FIG. 3, some components of the ophthalmologic apparatus 1 are omitted, and the components particularly necessary for describing the present embodiment are selectively shown.

(Controller)

The arithmetic and control unit 200 includes the controller 210, an image forming unit 220, and a data processor 230. The controller 210 includes, for example, a microprocessor, a RAM, a ROM, a hard disk drive, a communication interface, and the like. The controller 210 is provided with a main controller 211 and a storage unit 212.

The functions of the main controller 211 is implemented by a processor, for example. The storage unit 212 stores, in advance, a computer program for controlling the ophthalmologic apparatus. The computer program includes, for example, various light source control programs, optical scanner control program, various detector control programs, image forming program, data processing program, program for user interface, and the like. The main controller 211 operates according to the computer programs, and thereby the controller 210 performs the control processing.

(Main Controller)

The main controller 211 performs the various kinds of controls described above. In particular, as shown in FIG. 3, the main controller 211 controls components of the fundus camera unit 2 such as a focusing drivers 31A and 43A the CCD image sensors 35 and 38, the LCD 39, the optical path length changing unit 41, and the optical scanner 42. In addition, the main controller 211 controls an optical system driver 1A. Further, the main controller 211 controls components of the OCT unit 100 such as the light source unit 101, the optical path length changing unit 114, the detector 125, and the DAQ 130.

The focusing driver 31A moves the photography focusing lens 31 along an optical axis of the imaging optical system 30 under the control of the main controller 211. The focusing driver 31A is provided with a holding member that holds the photography focusing lens 31, an actuator that generates a driving force for moving the holding member, and a transmission mechanism that transmits the driving force from the actuator to the holding member. The actuator may be a pulse motor, for example. The transmission mechanism may include a combination of gears, a rack and pinion, and the like, for example. As a result, the focusing driver 31A controlled by the main controller 211 moves the photography focusing lens 31, thereby the focus position of the imaging optical system 30 is changed. Note that the focusing driver 31A may be configured to move the photography focusing lens 31 along the optical axis of the imaging optical system 30 in accordance with a manual operation or the user's operation on the operation unit 240B.

The focusing driver 43A moves the OCT focusing lens 43 along the optical axis of the interference optical system (the optical path of the measurement light) in the OCT unit 100 under the control of the main controller 211. The focusing driver 43A is provided with a holding member that holds the OCT focusing lens 43, an actuator that generates a driving force for moving the holding member, and a transmission mechanism that transmits the driving force from the actuator to the holding member. The actuator may be a pulse motor, for example. The transmission mechanism may include a combination of gears, a rack and pinion, and the like, for example. As a result, the focusing driver 43A controlled by the main controller 211 moves the OCT focusing lens 43, thereby the focus position of the measurement light is changed. Note that the focusing driver 43A may be configured to move the OCT focusing lens 43 along the optical axis of the interference optical system in accordance with a manual operation or the user's operation on the operation unit 240B.

The main controller 211 can control an exposure time (charge accumulation time), a sensitivity, a frame rate, or the like of the CCD image sensor 35. The main controller 211 can control an exposure time, a sensitivity, a frame rate, or the like of the CCD image sensor 38.

The main controller 211 can control the LCD 39 to display fixation targets or visual targets for the visual acuity measurement. Thereby, the visual target presented to the subject's eye E can be switched, or type of the visual targets can be changed. Further, the presentation position of the visual target to the subject's eye E can be changed by changing the display position of the visual target on the screen of the LCD 39.

The main controller 211 can control the optical path length changing unit 41 to change relatively the difference between the length of the optical path of the reference light LR and the length of the optical path of the measurement light LS. The main controller 211 controls the optical path length changing unit 41 so as to render a target site of the subject's eye E in a predetermined range in the frame of an OCT image. Specifically, the main controller 211 can control the optical path length changing unit 41 so as to render the target site of the subject's eye E in a predetermined z position (a position in the depth direction) in the frame of the OCT image.

The main controller 211 can control the optical scanner 42 to change a scanning position of the measurement light LS on the fundus Ef or the anterior segment of the subject's eye E.

The optical system driver 1A moves the optical system (the optical system shown in FIGS. 1 and 2) included in the ophthalmologic apparatus 1 three-dimensionally. The optical system driver 1A moves the optical system under the control of the main controller 211. This control is used in alignment and tracking. Here, tracking is to move the optical system of the apparatus according to the movement of the subject's eye E. To perform tracking, alignment and focusing are performed in advance. The tracking is performed by moving the optical system of the apparatus in real time according to the position and orientation of the subject's eye E based on the moving image obtained by imaging the subject's eye E, thereby maintaining a suitable positional relationship in which alignment and focusing are adjusted.

The main controller 211 can control the light source unit 101 to switch between lighting and non-lighting and to change light amount of the light L0, and the like.

The main controller 211 can control the optical path length changing unit 114 to change relatively the difference between the length of the optical path of the reference light LR and the length of the optical path of the measurement light LS. The main controller 211 controls the optical path length changing unit 114 so as to render a target site of the subject's eye E in a predetermined range in the frame of an OCT image. Specifically, the main controller 211 can control the optical path length changing unit 114 so as to render the target site of the subject's eye E in a predetermined z position in the frame of the OCT image. The main controller 211 can change relatively the difference between the length of the optical path of the reference light LR and the length of the optical path of the measurement light LS, by controlling at least one of the optical path length changing units 41 and 114. Hereinafter, a case will be described where the main controller 211 controls merely the optical path length changing unit 114 to adjust the difference of the optical path length between the measurement light LS and the reference light LR. However, the main controller 211 may control merely the optical path length changing unit 41 to adjust the difference of the optical path length between the measurement light LS and the reference light LR.

The main controller 211 can control an exposure time (charge accumulation time), a sensitivity, a frame rate, or the like of the detector 125. Further, the main controller 211 can control the DAQ 130.

When the front lens 23 is removed from between the subject's eye E and the objective lens 22, the main controller 211 performs control of tracking in a tracking mode for fundus. When the front lens 23 is arranged between the subject's eye E and the objective lens 22, the main controller 211 performs control of tracking in a tracking mode for anterior segment.

In the tracking mode for fundus, the main controller 211 performs control of tracking based on the fundus image of the subject's eye E acquired by the imaging optical system 30. The fundus images are acquired at different timings as a base image and a target image. The main controller 211 is capable of obtaining a misregistration amount (including a misregistration direction) of the target image, which is the anterior segment image obtained after acquiring the base image, with reference to the base image which is the anterior segment image of the subject's eye E obtained in advance, and of performing control of tracking based on the obtained misregistration amount. The misregistration amount of the target image with reference to the base image is obtained by using the phase only correlation (POC) processing. The main controller 211 can control the optical system driver 1A based on the obtained misregistration amount. The tracking mode for fundus using such the phase only correlation processing is similar to the processing disclosed in Japanese Unexamined Patent Application Publication No. 2015-043898. Thus, a detailed description will be omitted.

In the tracking mode for anterior segment, the main controller 211 performs control of tracking based on the anterior segment image of the subject's eye E acquired by the imaging optical system 30. The anterior segment images are acquired at different timings as a base image and a target image. The main controller 211 can perform control of tracking based on the misregistration amount between a partial image, which is an image of a predetermined region in the target image, and a corresponding partial image corresponding to a partial image in the base image. The misregistration amount of the partial image corresponding to the corresponding partial image is obtained by using the phase only correlation processing. The main controller 211 can control the optical system driver 1A based on the obtained misregistration amount.

(Storage Unit)

The storage unit 212 stores various types of data. Examples of the data stored in the storage unit 212 include, for example, image data of an OCT image, image data of a fundus image and an anterior segment image, and subject's eye information. The subject's eye information includes information on the subject such as patient ID and name, and information on the subject's eye such as identification information of the left eye/right eye. The storage unit 212 further stores data such as various types of programs and control information to run the ophthalmologic apparatus 1.

(Image Forming Unit)

The image forming unit 220 forms image data of tomographic images of the fundus Ef and the anterior segment based on detection signals from the detector 125 (DAQ 130). The image formation processing includes noise removal (noise reduction), filtering, fast Fourier transform (FFT), and the like. The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

Further, the image forming unit 220 can form an anterior segment image based on the detection result of the reflection light from the anterior segment of the subject's eye E obtained by the CCD image sensor 35 or the CCD image sensor 38.

The image forming unit 220 includes, for example, the circuitry described above. Incidentally, "image data" and an "image" based thereon may be treated in the same way in this specification. Further, a site of the subject's eye E and an image thereof may also be treated in the same way.

(Data Processor)

The data processor 230 performs various kinds of data processing (e.g., image processing) and various kinds of analysis processing on an image formed by the image forming unit 220. For example, the data processor 230 performs various correction processes such as brightness correction and dispersion correction of images.

The data processor 230 can form volume data (voxel data) of the subject's eye E by performing known image processing such as interpolation processing for interpolating pixels between tomographic images. In the case of displaying an image based on the volume data, the data processor 230 performs a rendering processing on the volume data so as to form a pseudo three-dimensional image viewed from a specific line-of-sight direction.

The data processor 230 can perform registration (i.e., position matching) between a fundus image (or an anterior segment image) and an OCT image. When the fundus image (or the anterior segment image) and the OCT image are obtained in parallel, the registration between the fundus image (or the anterior segment image) and the OCT image, which have been (almost) simultaneously obtained, can be performed using the optical axis of the imaging optical system 30 as a reference. Such registration can be achieved since the optical system for the fundus image (or the anterior segment image) and that for the OCT image are coaxial. Besides, regardless of the timing of obtaining the fundus image (or the anterior segment image) and that of the OCT image, the registration between the OCT image and the fundus image (or the anterior segment image) can be achieved by performing the registration between the fundus image (or the anterior segment image) and a front image formed by projecting at least part of an image area corresponding to the fundus Ef (or the anterior segment image) in the OCT image onto the xy plane. This registration method can also be employed when the optical system for acquiring fundus image (or the anterior segment image) and the optical system for OCT are not coaxial. Further, when both the optical systems are not coaxial, if the relative positional relationship between these optical systems is known, the registration can be performed with referring to the relative positional relationship in a manner similar to the case of coaxial optical systems.

Figure 4:
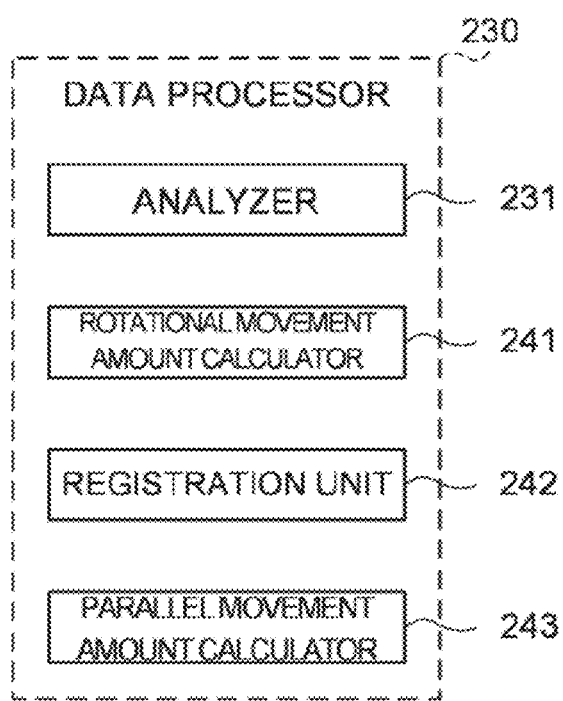
FIG. 4 is a schematic diagram illustrating an example of the configuration of a processing system of the ophthalmologic apparatus according to the embodiments.

As shown in FIG. 4, the data processor 230 includes an analyzer 231, a rotational movement amount calculator 241, a registration unit 242, and a parallel movement amount calculator 243.

Figure 5:
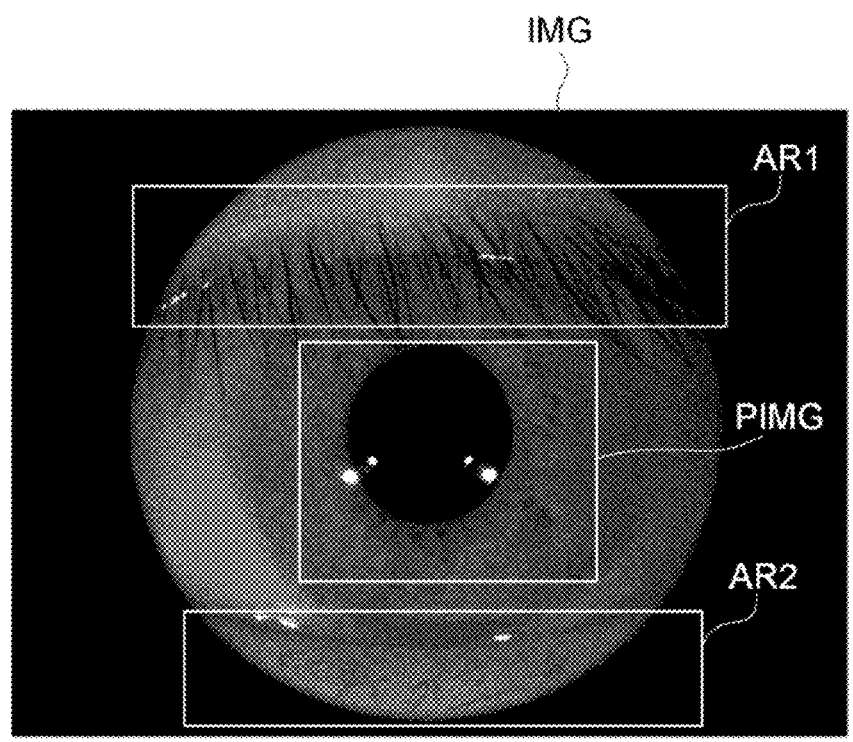
FIG. 5 is a schematic diagram for explaining the operation of the ophthalmologic apparatus of the embodiments.

As shown in FIG. 5, the analyzer 231 specifies the partial image PIMG from the target image IMG, the partial image PIMG being an image of the predetermined region. The analyzer 231 can specify the partial image PIMG in the target image IMG by analyzing the base image and the target image.

The analyzer 231 can specify an image of a region of which movement amount with respect to the base image is equal to or larger than a first threshold value in the target image as the partial image. For example, the analyzer 231 divides the target image into a plurality of regions, obtains the movement amount of the target image with respect to the base image for each region, and specifies an image of a region of which the obtained movement amount is equal to or larger than the first threshold value as the partial image. That is, the analyzer 231 specifies the image of the region which moves with respect to the base image as the partial image.

Alternatively, the analyzer 231 can specify a region (regions AR1 and AR2 in FIG. 5, for example) of which the movement amount with respect to the base image is equal to or less than a second threshold value in the target image and specify an image of a region removed the specified region from the target image, as the partial image. For example, the analyzer 231 divides the target image into a plurality of regions, obtains the movement amount of the target image with respect to the base image for each region, specifies an image of a region of which the obtained movement amount is equal to or less than the second threshold value, and specifies an image of a region removed the specified region from the target image, as the partial image. That is, the analyzer 231 specifies the region which does not move with respect to the base image and specifies the image of the region removed the specified region from the target image as the partial image.

Alternatively, the analyzer 231 can specify a region (regions AR1 and AR2 in FIG. 5, for example) in which an eyelid (upper eyelid, lower eyelid) is represented in the target image, and specifies an image of a region removed the specified region from the target image, as the partial image. For example, the analyzer 231 specifies a region including a form corresponding to the eyelid or the eyelash from brightness information for each pixel in the target image, and specifies an image of a region removed the specified region from the target image, as the partial image.

Alternatively, the analyzer 231 can specify an image of a predetermined region in the target image as the partial image. The predetermined region may include a region corresponding to the pupil of the subject's eye E and may be a region in which the upper eyelid, the lower eyelid, and the eyelash of the subject's eye are not represented. For example, the analyzer 231 extracts a predetermined region from the target image and specifies the extracted image as the partial image. That is, the analyzer 231 specifies an image of the region cut out from the target image so that the angle of view becomes narrow, as the partial image.

As described above, in the specified partial image, the region corresponding to the pupil of the subject's eye E is represented and the upper eyelid, the lower eyelid, and the eyelash of the subject's eye E are not represented.

It should be noted that the analyzer 231 may specify the partial image in the target image base on an image of a predetermined region in the base image. For example, the analyzer 231 specifies the partial image in the target image from the image of the region corresponding to the pupil of the subject's eye E in the base image.

The analyzer 231 specifies a corresponding partial image in the base image corresponding to the partial image specified as described above.

(Tracking Mode for Fundus)

The data processor 230 obtains a misregistration amount between the base image and the target image, and outputs information corresponding to the obtained misregistration amount to the controller 210 (the main controller 211). The misregistration amount includes a rotational movement amount at sub-pixel level (less than 1 pixel) in a rotation direction (rotation direction around the axis in the z direction) between the base image and the target image, a rotational movement direction thereof, a parallel movement amount at sub-pixel level in the xy plane between the base image and the target image, and a parallel movement direction thereof, and the like.

In particular, the data processor 230 calculates a rotational movement amount and a rotational movement direction between the base image and the target image at the sub-pixel level, and performs registration between the base image and the target image in the rotation direction based on the calculated rotational movement amount and the calculated rotational movement direction. The data processor 230 then calculates a parallel movement amount and a parallel movement direction between the base image and the target image, which have been registered to each other, at the sub-pixel level.

The rotational movement amount calculator 241 and the parallel movement amount calculator 243 obtain a misregistration (displacement) (including misregistration amount and misregistration direction) of the target image with respect to the base image based on the base image and the target image as described above. The registration unit 242 performs registration (i.e., position matching) between the base image and the target image.

The rotational movement amount calculator 241 calculates a rotational movement amount and a rotational movement direction between the base image and the target image. The rotational movement amount calculator 241 performs a phase only correlation processing on the base image and the target image to obtain the rotational movement amount and the rotational movement direction between the base image and the target image. Such the phase only correlation processing is similar to the processing disclosed in Japanese Unexamined Patent Application Publication No. 2015-043898.

(Tracking Mode for Anterior Segment)

The data processor 230 obtains a misregistration amount between the corresponding partial image in the base image and the partial image in the target image, and outputs information corresponding to the obtained misregistration amount to the controller 210 (the main controller 211). The misregistration amount includes a rotational movement amount at sub-pixel level (less than 1 pixel) in a rotation direction (rotation direction around the axis in the z direction) between the corresponding partial image and the partial image, a rotational movement direction thereof, a parallel movement amount at sub-pixel level in the xy plane between the corresponding partial image and the partial image, and a parallel movement direction thereof, and the like.

In particular, the data processor 230 calculates a rotational movement amount and a rotational movement direction between the corresponding partial image and the partial image at the sub-pixel level, and performs registration between the corresponding partial image and the partial image in the rotation direction based on the calculated rotational movement amount and the calculated rotational movement direction. The data processor 230 then calculates a parallel movement amount and a parallel movement direction between the corresponding partial image and the partial image, which have been registered to each other, at the sub-pixel level.

The rotational movement amount calculator 241 and the parallel movement amount calculator 243 obtain a misregistration (displacement) (including misregistration amount and misregistration direction) of the partial image with respect to the corresponding partial image based on the corresponding partial image and the partial image as described above. The registration unit 242 performs registration (i.e., position matching) between the corresponding partial image and the partial image.

The rotational movement amount calculator 241 calculates a rotational movement amount and a rotational movement direction between the corresponding partial image and the partial image. The rotational movement amount calculator 241 can perform the phase only correlation processing on the corresponding partial image and the partial image to calculate the rotational movement amount and the rotational movement direction between the corresponding partial image and the partial image. Such the phase only correlation processing is similar to the processing disclosed in Japanese Unexamined Patent Application Publication No. 2015-043898.

In the phase only correlation processing according to the embodiments, for example, the following phase only correlation function is used. Hereinafter, the case of the tracking mode for fundus will be mainly described. However, it is possible to apply to the tracking mode for anterior segment by replacing the base image with the "corresponding partial image" and replacing the target image with the "partial image".

First, it is assumed that the corresponding partial image (the base image) and the partial image (the target image) having an image size of $N_1 \times N_2$ ($N_1$ and $N_2$ are positive integers) are represented by $f(n_1, n_2)$ and $g(n_1, n_2)$, respectively. It is also assumed herein that, in the discrete space, $n_1 = -M_1, \ldots, M_1$, $N_1 = 2M_1 + 1$ ($M_1$ is a positive integer), and the result of two-dimensional discrete Fourier transform (DFT) of $f(n_1, n_2)$ is $F(k_1, k_2)$. Then, $F(k_1, k_2)$ is represented by Equation (1) as follows:

[Equation 1]

$$F(k_1, k_2) = \sum_{n_1=-M_1}^{M_1} \sum_{n_2=-M_2}^{M_2} f(n_1, n_2) W_{N_1}^{k_1 n_1} W_{N_2}^{k_2 n_2} = A_F(k_1, k_2) e^{j\theta_F(k_1, k_2)} \quad (1)$$

$$\left( k_1 = -M_1, \ldots, M_1, k_2 = -M_2, \ldots, M_2, W_{N_1} = e^{-j\frac{2\pi}{N_1}}, W_{N_2} = e^{-j\frac{2\pi}{N_2}} \right)$$

In Equation (1), $A_F(k_1, k_2)$ is the amplitude component of $f(n_1, n_2)$, and $e^{j\theta F(k1, k2)}$ is the phase component of $f(n_1, n_2)$.

Similarly, it is assumed that, in the discrete space, $n_2=-M_2, \ldots, M_2$, $N_2=2M_2+1$ ($M_2$ is a positive integer), and the result of two-dimensional DFT of $g(n_1, n_2)$ is $G(k_1, k_2)$. Then, $G(k_1, k_2)$ is represented by Equation (2) as follows:

[Equation 2]

$$G(k_1, k_2) = \sum_{n_1=-M_1}^{M_1} \sum_{n_2=-M_2}^{M_2} g(n_1, n_2) W_{N_1}^{k_1 n_1} W_{N_2}^{k_2 n_2} = A_G(k_1, k_2) e^{j\theta G(k_1, k_2)} \quad (2)$$

$$\left(k_1 = -M_1, \ldots, M_1, k_2 = -M_2, \ldots, M_2, W_{N_1} = e^{-j\frac{2\pi}{N_1}}, W_{N_2} = e^{-j\frac{2\pi}{N_2}}\right)$$

In Equation (2), $A_G(k_1, k_2)$ is the amplitude component of $g(n_1, n_2)$, and $e^{j\theta G(k1, k2)}$ is the phase component of $g(n_1, n_2)$.

Using Equations (1) and (2), the phase only synthesis function used in the phase only synthesis processing is defined by Equation (3) as follows:

[Equation 3]

$$\hat{R}(k_1, k_2) = \frac{F(k_1, k_2)\overline{G(k_1, k_2)}}{|F(k_1, k_2)\overline{G(k_1, k_2)}|} = e^{j\theta(k_1, k_2)} \quad (3)$$

By applying a two-dimensional inverse discrete Fourier transform (IDFT) to the phase only synthesis function represented by Equation (3), the phase only correlation function according to the embodiments is represented by Equation (4) as follows:

[Equation 4]

$$\hat{r}(n_1, n_2) = \frac{1}{N_1 N_2} \sum_{k_1=-M_1}^{M_1} \sum_{k_2=-M_2}^{M_2} \hat{R}(k_1, k_2) W_{N_1}^{-k_1 n_1} W_{N_2}^{-k_2 n_2} \quad (4)$$

An image obtained by shifting a two-dimensional image $s_c(x_1, x_2)$ defined in a continuous space by a minute movement amount $\delta_1$ in the $x_1$ direction and by a minute movement amount $\delta_2$ in the $x_2$ direction is represented as $s_c(x_1-\delta_1, x_2-\delta_2)$. The two-dimensional image $f(n_1, n_2)$ sampled at a sampling interval $T_1$ in the discrete space is defined by Equation (5) as follows:

[Equation 5]

$$f(n_1, n_2) = s_c(x_1, x_2)|_{x_1=n_1 T_1, x_2=n_2 T_2} \quad (5)$$

Similarly, the two-dimensional image $g(n_1, n_2)$ sampled at a sampling interval $T_2$ in the discrete space is defined by Equation (6) as follows:

[Equation 6]

$$g(n_1, n_2) = s_c(x_1-\delta_1, x_2-\delta_2)|_{x_1=n_1 T_1, x_2=n_2 T_2} \quad (6)$$

In Equations (5) and (6), and $n_1=-M_1, \ldots, M_1$, $n_2=-M_2, \ldots, M_2$. Thus, the phase only correlation function related to the two-dimensional images $f(n_1, n_2)$ and $g(n_1, n_2)$ in the discrete space is represented in general form as Equation (7) as follows:

[Equation 7]

$$\hat{r}(n_1, n_2) \approx \frac{\alpha}{N_1 N_2} \frac{\sin\{\pi(n_1 + \delta_1)\}}{\sin\left\{\frac{\pi}{N_1}(n_1 + \delta_1)\right\}} \frac{\sin\{\pi(n_2 + \delta_2)\}}{\sin\left\{\frac{\pi}{N_2}(n_2 + \delta_2)\right\}} \quad (7)$$

Figure 6:
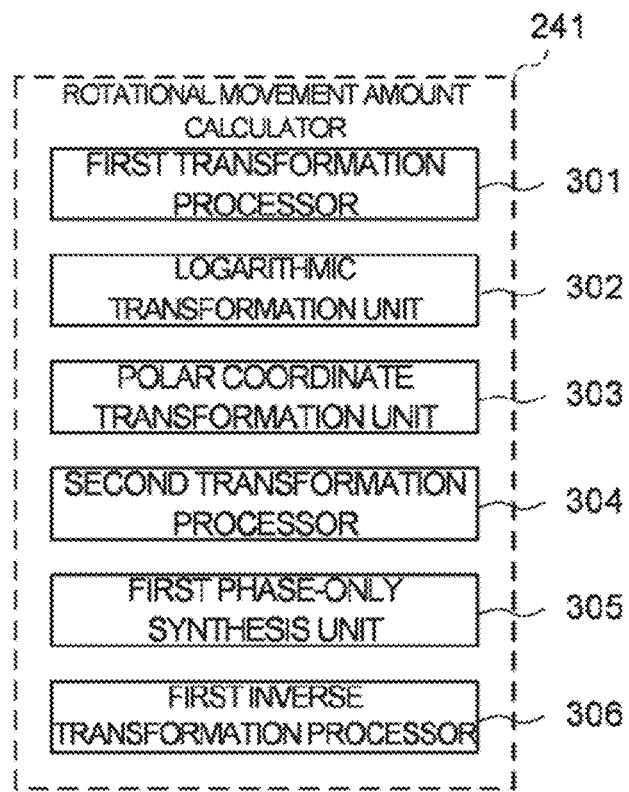
FIG. 6 is a schematic diagram illustrating an example of the configuration of a processing system of the ophthalmologic apparatus according to the embodiments.

As shown in FIG. 6, the rotational movement amount calculator 241 includes a first transformation processor 301, a logarithmic transformation unit 302, a polar coordinate transformation unit 303, a second transformation processor 304, a first phase-only synthesis unit 305, and a first inverse transformation processor 306.

The first transformation processor 301 performs a two-dimensional DFT processing on the corresponding partial image (the base image). The first transformation processor 301 performs the two-dimensional DFT processing also on the partial image (the target image). The two-dimensional DFT processing performed by the first transformation processor 301 includes two-dimensional DFT, and a known shift processing for shifting the quadrant with respect to the result of the two-dimensional DFT. Hereinafter, this shift processing may be referred to as "shift". Note that the two-dimensional DFT performed by the first transformation processor 301 may be two-dimensional FFT.

The logarithmic transformation unit 302 applies a logarithmic transformation to the calculation result for the corresponding partial image (the base image) obtained by the first transformation processor 301. Further, the logarithmic transformation unit 302 applies a logarithmic transformation also to the calculation result for the partial image (the target image) obtained by the first transformation processor 301. The logarithmic transformation performed by the logarithmic transformation unit 302 has the effect of compressing the amplitude spectrum that has a tendency to concentrate in the low-frequency region of the spatial frequency in a natural image.

The polar coordinate transformation unit 303 applies a polar coordinate transformation to the calculation result for the corresponding partial image (the base image) obtained by the logarithmic transformation unit 302. Further, the polar coordinate transformation unit 303 applies a polar coordinate transformation also to the calculation result for the partial image (the target image) obtained by the logarithmic transformation unit 302. When the logarithmic transformation is not performed by the logarithmic transformation unit 302, the polar coordinate transformation unit 303 applies a polar coordinate transformation to the calculation results for the corresponding partial image and the partial image obtained by the first transformation processor 301. The polar coordinate transformation performed by the polar coordinate transformation unit 303 is the processing of converting the movement amount in the rotation direction into the movement amount in the parallel direction ($n_1$ direction, $n_2$ direction) in Equations (1) to (7).

As illustrated in Equation (1), the second transformation processor 304 performs the two-dimensional DFT processing (two-dimensional DFT+shift) on the calculation result for the corresponding partial image (the base image) obtained by the polar coordinate transformation unit 303. Prior to the arithmetic processing of the first phase-only synthesis unit 305, the processing result of the corresponding partial image obtained by the second transformation processor 304 is stored in, for example, the storage unit 212 in advance as the base POC data normalized by the amplitude component. As illustrated in Equation (2), the second transformation processor 304 performs the two-dimensional DFT processing (two-dimensional DFT+shift) on the calculation result for the partial image (the target image) obtained by the polar coordinate transformation unit 303. Incidentally, the two-dimensional DFT performed by the second transformation processor 304 may also be two-dimensional FFT.

As illustrated in Equation (3), the first phase-only synthesis unit 305 performs a phase only synthesis processing for synthesizing the base POC data (first data) previously obtained for the corresponding partial image (the base image) and the target POC data (second data) normalized by the amplitude component based on the calculation result for the target image obtained by the second transformation processor 304.

The first inverse transformation processor 306 performs a two-dimensional IDFT processing on the calculation result obtained by the first phase-only synthesis unit 305. The two-dimensional IDFT processing performed by the first inverse transformation processor 306 includes two-dimensional IDFT, and a known shift processing for shifting the quadrant with respect to the result of the two-dimensional IDFT. Note that the two-dimensional IDFT may be a two-dimensional inverse fast Fourier transform (IFFT).

The rotational movement amount calculator 241 calculates a rotational movement amount and a rotational movement direction based on the calculation result obtained by the first inverse transformation processor 306. Specifically, the rotational movement amount calculator 241 specifies the peak position based on the calculation result obtained by the first inverse transformation processor 306 to thereby calculate the rotational movement amount and the rotational movement direction at the pixel level. The rotational movement amount calculator 241 then specifies the pixel position at which the correlation value of the phase only correlation function represented by Equation (7) becomes the maximum in the vicinity of the peak position specified at the pixel level, thereby obtaining the rotational movement amount and the rotational movement direction at the sub-pixel level.

The rotational movement amount calculator 241 need not necessarily calculate the rotational movement amount and the rotational movement direction through the phase only correlation processing. The rotational movement amount calculator 241 may calculate the rotational movement amount by a known technique, and output the rotational movement amount and the rotational movement direction.

The parallel movement amount calculator 243 calculates a parallel movement amount and a parallel movement direction between the corresponding partial image (the base image) and the partial image (the target image) registered by the registration unit 242 described later. The parallel movement amount calculator 243 performs a phase only correlation processing on the corresponding partial image and the partial image registered by the registration unit 242 to calculate a parallel movement amount and a parallel movement direction between the corresponding partial image and the partial image. Such the phase only correlation processing is similar to the processing disclosed in Japanese Unexamined Patent Application Publication No. 2015-043898.

The parallel movement amount calculator 243 calculates a parallel movement amount and a parallel movement direction between the corresponding partial image and the partial image registered by the registration unit 242. In particular, the parallel movement amount calculator 243 performs a phase only correlation processing on the corresponding partial image and the partial image registered by the registration unit 242 to calculate the parallel movement amount and the parallel movement direction between the corresponding partial image and the partial image.

Figure 7:
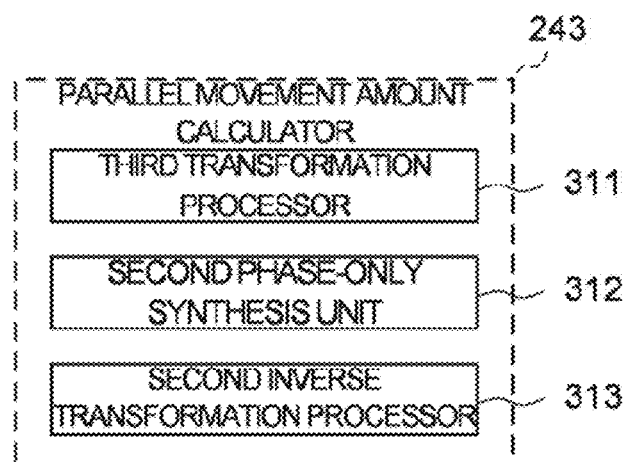
FIG. 7 is a schematic diagram illustrating an example of the configuration of a processing system of the ophthalmologic apparatus according to the embodiments.

As shown in FIG. 7, the parallel movement amount calculator 243 includes a third transformation processor 311, a second phase-only synthesis unit 312, and a second inverse transformation processor 313.

As illustrated in Equation (1), the third transformation processor 311 performs the two-dimensional DFT processing (two-dimensional DFT+shift) on the corresponding partial image (the base image). Prior to the arithmetic processing of the second phase-only synthesis unit 312, the processing results of the corresponding partial image obtained by the third transformation processor 311 is stored in, for example, the storage unit 212 in advance as the base POC data (third data) normalized by amplitude component. As illustrated in Equation (2), the third transformation processor 311 performs the two-dimensional DFT processing (two-dimensional DFT+shift) on the partial image (the target image). Incidentally, the two-dimensional DFT performed by the third transformation processor 311 may also be two-dimensional FFT.

As illustrated in Equation (3), the second phase-only synthesis unit 312 performs a phase only synthesis processing for synthesizing the base POC data (third data) previously obtained for the corresponding partial image (the base image) and the target POC data (fourth data) normalized by amplitude component based on the calculation result for the partial image (the target image) obtained by the third transformation processor 311.

The second inverse transformation processor 313 performs a two-dimensional IDFT processing (two-dimensional IDFT+shift) on the calculation result obtained by the second phase-only synthesis unit 312. The two-dimensional IDFT performed by the second inverse transformation processor 313 may be two-dimensional IFFT.

The parallel movement amount calculator 243 calculates a parallel movement amount and a parallel movement direction based on the calculation result obtained by the second inverse transformation processor 313. Specifically, the parallel movement amount calculator 243 specifies the peak position based on the calculation result obtained by the second inverse transformation processor 313 to thereby obtain the parallel movement amount and the parallel movement direction at the pixel level. The parallel movement amount calculator 243 then specifies the pixel position at which the correlation value of the phase only correlation function represented by Equation (7) becomes the maximum in the vicinity of the peak position specified at the pixel level, thereby obtaining the parallel movement amount and the parallel movement direction at the sub-pixel level.

The registration unit 242 performs registration in the rotation direction between the corresponding partial image and the partial image based on the rotational movement amount and the rotational movement direction calculated by the rotational movement amount calculator 241. Specifically, the registration unit 242 registers the partial image with reference to the corresponding partial image in the rotation direction based on the rotational movement amount and the rotational movement direction calculated by the rotational movement amount calculator 241. Incidentally, the registration unit 242 may register the corresponding partial image with reference to the partial image in the rotation direction based on the rotational movement amount and the rotational movement direction calculated by the rotational movement amount calculator 241.

The data processor 230 that functions as above includes, for example, a microprocessor, a RAM, a ROM, a hard disk drive, a circuit board, and the like. In a storage device such as the hard disk drive, a computer program for causing the microprocessor to execute the functions described above is stored in advance.

(User Interface)

A user interface 240 includes the display unit 240A and the operation unit 240B. The display unit 240A includes the aforementioned display device of the arithmetic and control unit 200 and the display device 3. The operation unit 240B includes the aforementioned operation device of the arithmetic and control unit 200. The operation unit 240B may include various types of buttons and keys provided on the case of the ophthalmologic apparatus 1 or the outside. Besides, the display unit 240A may include various types of displays such as a touch panel and the like arranged on the case of the fundus camera unit 2.

Note that the display unit 240A and the operation unit 240B need not necessarily be formed as separate devices. For example, a device like a touch panel, which has a display function integrated with an operation function, can be used. In such cases, the operation part 240B includes the touch panel and a computer program. The content of operation performed on the operation unit 240B is fed to the controller 210 in the morphology of an electrical signal. Moreover, operations and inputs of information may be performed by using a graphical user interface (GUI) displayed on the display unit 240A and the operation unit 240B.

The optical system 100 (specifically, the interference optical system included in the imaging optical system 30 or the OCT unit 100) as shown in FIG. 1 is an example of the "optical system" according to the embodiments. The CCD image sensor 35 is an example of the "image acquiring unit" according to the embodiments. The base image is an example of the "first image" according to the embodiments. The target image is an example of the "second image" according to the embodiments. The optical system driver 1A is an example of the "movement mechanism" according to the embodiments. The analyzer 231 is an example of the "specifying unit" according to the embodiments.

[Operation Example]

Described below is an example of the operation of the ophthalmologic apparatus according to the embodiments.

Figure 8:
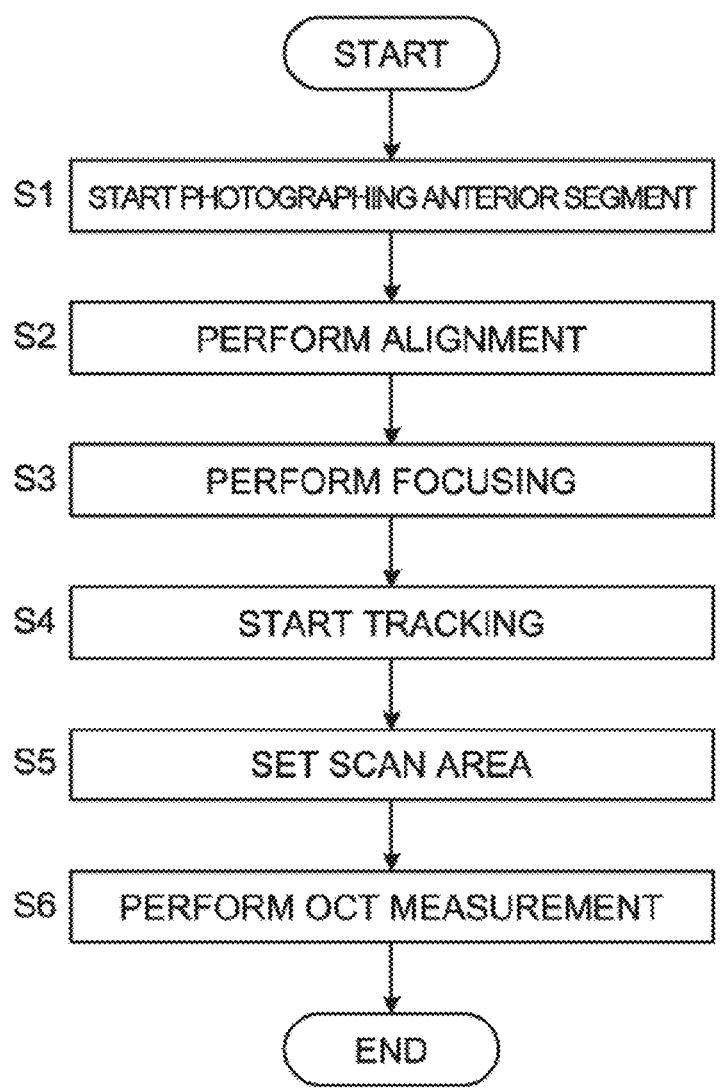
FIG. 8 is a flow chart of an operation example of the ophthalmologic apparatus according to the embodiments.

FIG. 8 shows a flow chart of an operation example of the ophthalmologic apparatus 1 according to the embodiments. In FIG. 8, the front lens 23 is arranged between the subject's eye E and the objective lens 22.

(S1: Start Photographing Anterior Segment)

First, the anterior segment is continuously irradiated with the illumination light from the observation light source 11 (near-infrared light through the action of the visible cut filter 14), thereby starting the acquisition of a near-infrared moving image of the anterior segment. The near-infrared moving image is acquired in real time until the end of the continuous illumination. The frames of the moving image are temporarily stored in a frame memory (the storage unit 212) and sequentially sent to the data processor 230.

Incidentally, the alignment indicator and the split target are projected onto the eye E respectively by the alignment optical system 50 and the focus optical system 60. Accordingly, the alignment indicator and the split target are illustrated in the near-infrared moving image. Alignment and focusing can be performed using them. The fixation target is also projected onto the subject's eye E by the LCD 39. The subject is instructed to fixate the eye on the fixation target.

(S2: Perform Alignment)

The data processor 230 sequentially analyzes the frames successively acquired by shooting a moving image of the subject's eye E with the optical system to find the position of the alignment indicator, thereby calculating the movement amount of the optical system. The controller 210 controls the optical system driver 1A based on the movement amount of the optical system obtained by the data processor 230 to perform automatic alignment.

(S3: Perform Focusing)

The data processor 230 sequentially analyzes the frames successively acquired by shooting a moving image of the subject's eye E with the optical system to find the position of the split target, thereby calculating the movement amount of the photography focusing lens 31 and the OCT focusing lens 43. The controller 210 controls the focusing drivers 31A and 43A based on the movement amount of the photography focusing lens 31 and the OCT focusing lens 43 obtained by the data processor 230 to perform automatic focusing.

S3: Start Tracking

Subsequently, the controller 210 starts the control for automatic tracking. Specifically, the data processor 230 analyzes the frames successively acquired by shooting a moving image of the subject's eye E with the optical system in real time, and monitors the movement (positional change) of the subject's eye E. The controller 210 controls the optical system driver 1A to move the optical system in accordance with the position of the subject's eye E sequentially obtained. Thereby, the optical system can follow the movement of the subject's eye E in real time. Thus, it is possible to maintain a good positional relationship with proper alignment and focus.

When the front lens 23 is removed from between the subject's eye E and the objective lens 22, the controller 210 performs control of tracking in the tracking mode for fundus as described above. That is, the data processor 230 sequentially calculates a misregistration amount at the sub-pixel level between the base image and the target image. The controller 210 moves the optical system to correct the misregistration amount calculated by the data processor 230 for each frame or every a plurality of frames.

When the front lens 23 is arranged between the subject's eye E and the objective lens 22, the controller 210 performs control of tracking in the tracking mode for anterior segment as described above. That is, the data processor 230 sequentially calculates a misregistration amount at the sub-pixel level between the corresponding partial image and the partial image. The controller 210 moves the optical system to correct the misregistration amount calculated by the data processor 230 for each frame or every a plurality of frames.

(S5: Set Scan Area)

The controller 210 displays the near-infrared moving image on the display unit 240A in real time. The user sets a scan area on the near-infrared moving image using the operation part 240B. The scan area may be one- or two-dimensional.

(S6: Perform OCT Measurement)

The controller 210 controls a light source unit 101 and the optical path length changing unit 41 as well as controlling the optical scanner 42 based on the scan area set in step S5 to perform OCT measurement of the anterior segment. The image forming unit 220 forms a tomographic image of the anterior segment based on a detection signal obtained. If three-dimensional scan is set as the scan mode, the data processor 230 forms a three-dimensional image of the anterior segment based on a plurality of tomographic images formed by the image forming unit 220. Then, the operation example is completed (END).

The following describes a processing example for the control of the tracking. The control of the tracking in the tracking mode for fundus is similar to the processing disclosed in Japanese Unexamined Patent Application Publication No. 2015-043898. Thus, a detailed description will be omitted. Hereinafter, the processing example of the control of the tracking in the tracking mode for anterior segment will be mainly described.

Figure 9:
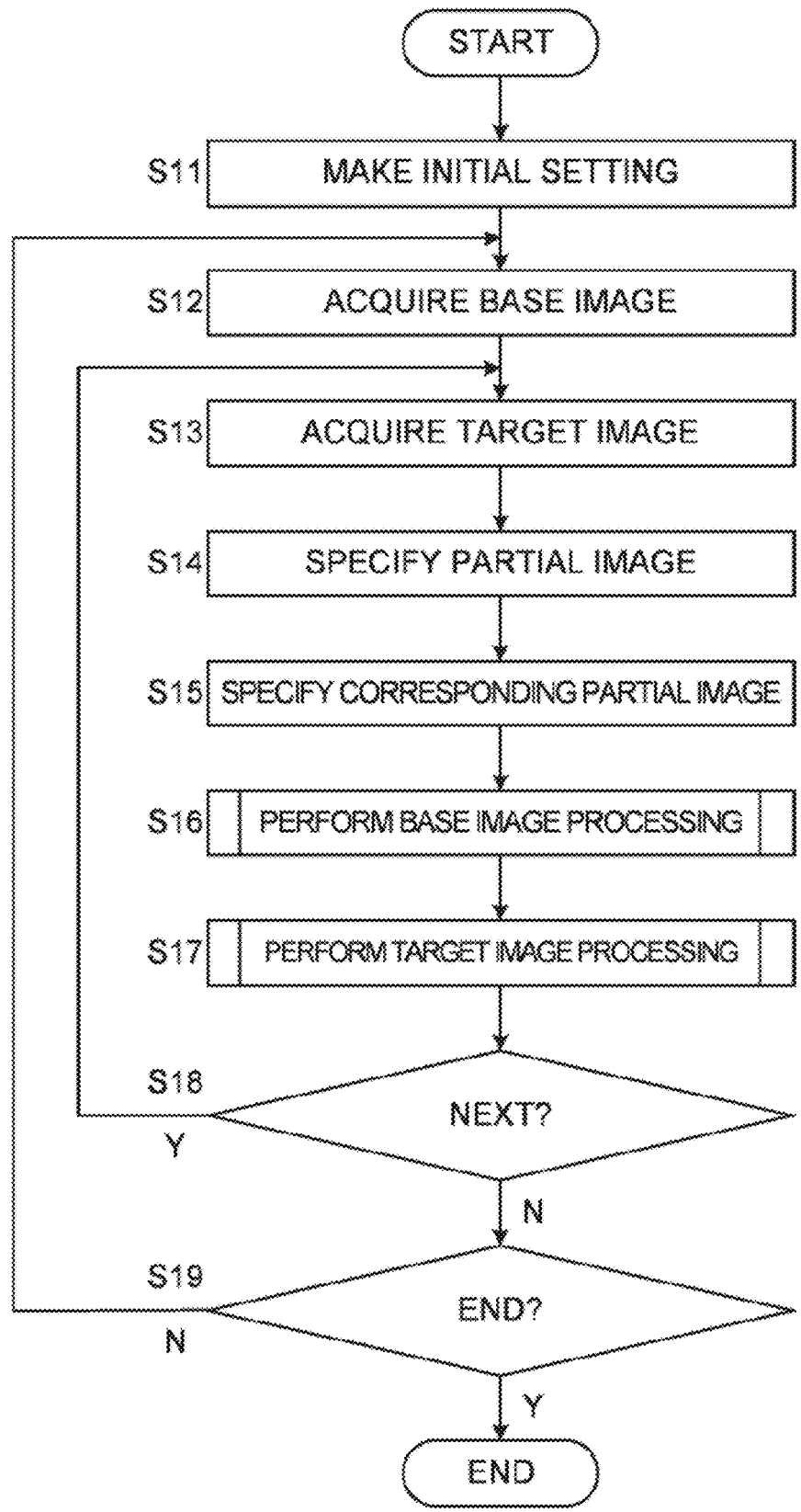
FIG. 9 is a flow chart of an operation example of the ophthalmologic apparatus according to the embodiments.

FIG. 9 shows a flow chart of a processing example of the control of the tracking in the tracking mode for anterior segment according to the embodiments. For example, when the subject's eye is changed or the imaging mode is changed, the processing shown in FIG. 9 is performed.

(S11: Make Initial Setting)

First, the main controller 211 performs a predetermined initialization processing. Examples of the initialization processing include securing resources, setting the scan area for acquiring the base image or the target image, initializing the data processor 230, and the like.

(S12: Acquire Base Image)

Next, the main controller 211 controls the imaging optical system 30 to photograph the anterior segment of the subject's eye E. Thereby, the base image is acquired. The acquired base image is stored in the storage unit 212.

(S13: Acquire Target Image)

Subsequently, after acquiring the base image, the main controller 211 controls the imaging optical system 30 to photograph the anterior segment of the subject's eye E. Thereby, the target image is acquired. The acquired target image is stored in the storage unit 212.

(S14: Specify Partial Image)

Next, the main controller 211 controls the analyzer 231 to specify a partial image in the target image acquired in step S13. As described above, the analyzer 231 specifies the partial image where the region corresponding to the pupil of the subject's eye E is represented and the upper eyelid, the lower eyelid, and the eyelash of the subject's eye E are not represented.

(S15: Specify Corresponding Partial Image)

The main controller 211 controls the analyzer 231 to specify a corresponding partial image corresponding to the partial image specified in step S14 from the base image acquired in step S12.

(S16: Perform Base Image Processing)

Next, the main controller 211 controls the data processor 230 to perform the base image processing for the performing the phase only correlation processing on the corresponding partial image specified in step S15. The base image processing is described in detail later.

(S17: Perform Target Image Processing)

Sequentially, the main controller 211 controls the data processor 230 to perform the target image processing for performing the phase only correlation processing on the partial image specified in step S14. In the target image processing, the processing for the control of the tracking based on the corresponding partial image specified in step S15 and the partial image specified in step S14 is performed. The target image processing is described in detail later.

(S18: Next?)

The main controller 211 determines the presence or absence of a target image to be processed next. When it is determined the presence of the target image to be processed next (S18: Y), the operation of the ophthalmologic apparatus 1 moves to step S13. When it is determined the absence of the target image to be processed next (S18: N), the operation of the ophthalmologic apparatus 1 moves to step S19.

(S19: END?)

When it is determined the absence of the target image to be processed next in step S18 (S18: N), the main controller 211 determines whether to end the photographing or not. When it is determined that the photographing is not to be ended (S19: N), the operation of the ophthalmologic apparatus 1 moves to step S12. When it is determined that the photographing is to be ended (S19: Y), the ophthalmologic apparatus 1 terminates the processing for the control of the tracking (END).

Next, a description is given in detail of the base image processing in step S16.

Figure 10:
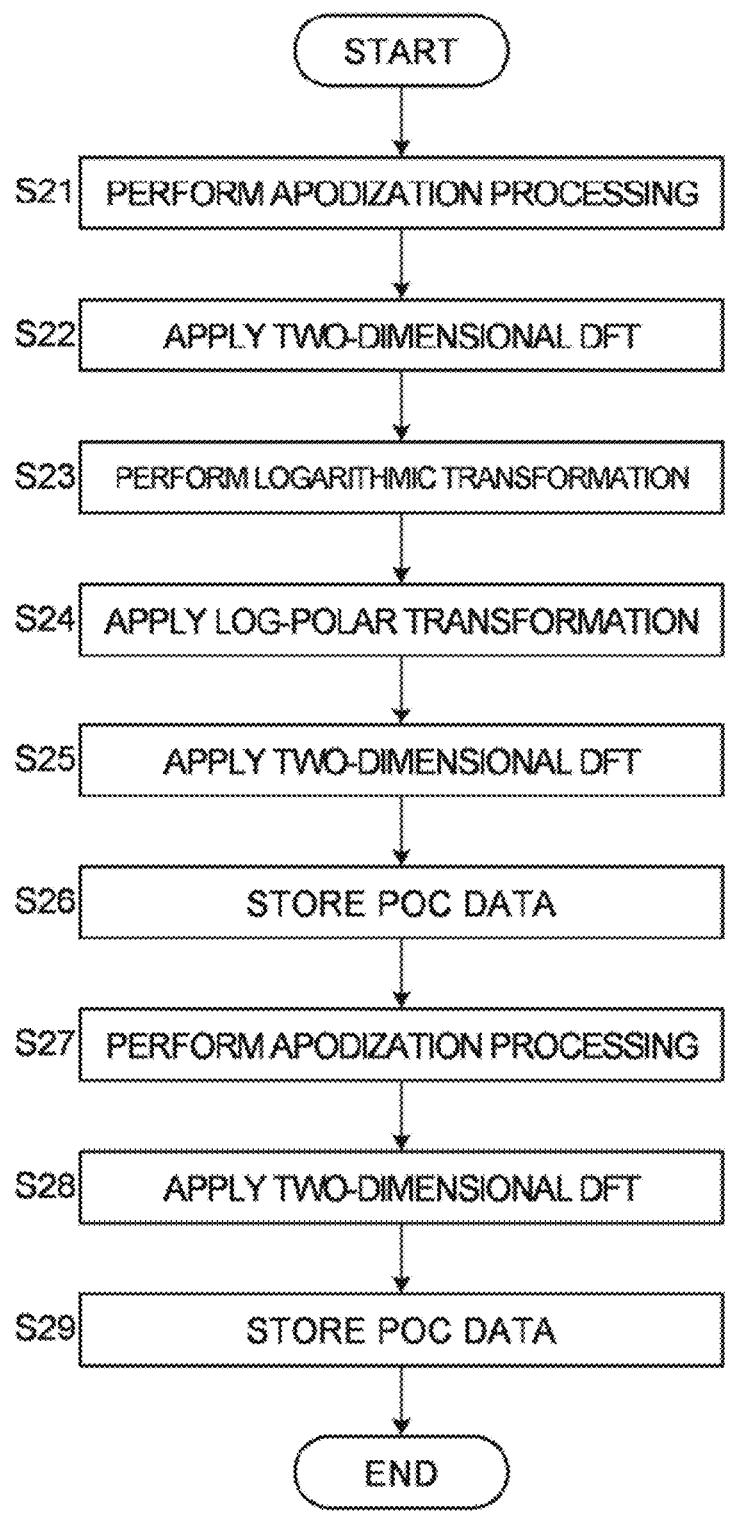
FIG. 10 is a flow chart of an operation example of the ophthalmologic apparatus according to the embodiments.

FIG. 10 illustrates an example of a flow of the base image processing according to the embodiments.

(S21: Perform Apodization Processing)

First, the rotational movement amount calculator 241 performs an apodization processing on the corresponding partial image (the base image). The apodization processing is a processing to increase the dynamic range through multiplication by an apodization function to reduce the amplitude of side lobes as well as suppressing to some extent a decrease in the amplitude of the main lobe. Examples of the apodization function include window functions such as a known Hanning window, Gaussian window, rectangular window, and the like. The apodization processing is performed by, for example, an apodization processor (not illustrated) in the first transformation processor 301 or the rotational movement amount calculator 241.

(S22: Apply Two-Dimensional DFT)

Next, the first transformation processor 301 applies a two-dimensional DFT to the result of the apodization processing performed on the corresponding partial image in step S21.

(S23: Perform Logarithmic Transformation)

Next, the logarithmic transformation unit 302 applies a logarithmic transformation to the processing result of the two-dimensional DFT in step S22. The logarithmic transformation is represented by Equation (8) as follows: where Re is the real component of the result of the two-dimensional DFT, Im is the imaginary component thereof, and Am is the result of the logarithmic transformation. This compresses the amplitude spectrum that tends to be concentrated in the low-frequency region of spatial frequencies in a natural image.

[Equation 8]

$$Am = 20 \times \log_{10}(\sqrt{Re^2 + Im^2} + 1) \tag{8}$$

(S24: Apply Log-Polar Transformation)

Next, the polar coordinate transformation unit 303 applies a Log-Polar transformation to the processing result of the logarithmic transformation in step S23. Thus, the radial direction is changed to the x direction, and the argument direction is changed to the y direction.

(S25: Apply Two-Dimensional DFT)

Next, the second transformation processor 304 applies a two-dimensional DFT to the processing result of the Log-Polar transformation in step S24.

(S26: Store POC Data)

Next, the rotational movement amount calculator 241 performs normalization with the amplitude component based on the processing result of the two-dimensional DFT in step S25, and stores it in the storage unit 212 as first base POC data based on the processing result of the two-dimensional DFT. Here, the first base POC data stored in the storage unit 212 is used to calculate a correlation value of the phase only correlation function for calculating the rotational movement amount and the rotational movement direction.

(S27: Perform Apodization Processing)

Subsequently, the parallel movement amount calculator 243 generates base POC data used to calculate a correlation value of the phase only correlation function for calculating a parallel movement amount and a parallel movement direction with respect to the corresponding partial image. Here, the parallel movement amount calculator 243 performs the apodization processing on the corresponding partial image. The apodization processing is performed in the same manner as described for step S21. If the processing result of step S21 is stored in the storage unit 212, step S27 can be dispensed with.

(S28: Apply Two-Dimensional DFT)

Next, the third transformation processor 311 applies a two-dimensional DFT to the real component of the result of the apodization processing performed on the corresponding partial image.

(S29: Store POC Data)

Next, the parallel movement amount calculator 243 performs normalization with the amplitude component based on the processing result of the two-dimensional DFT, and stores it in the storage unit 212 as second base POC data based on the processing result of the two-dimensional DFT. Here, the second base POC data stored in the storage unit 212 is used to calculate a correlation value of the phase only correlation function for calculating a parallel movement amount and a parallel movement direction. With this, a series of processes of the base image processing is completed (END).

Next, a description is given in detail of the target image processing in step S17.

Figure 11:
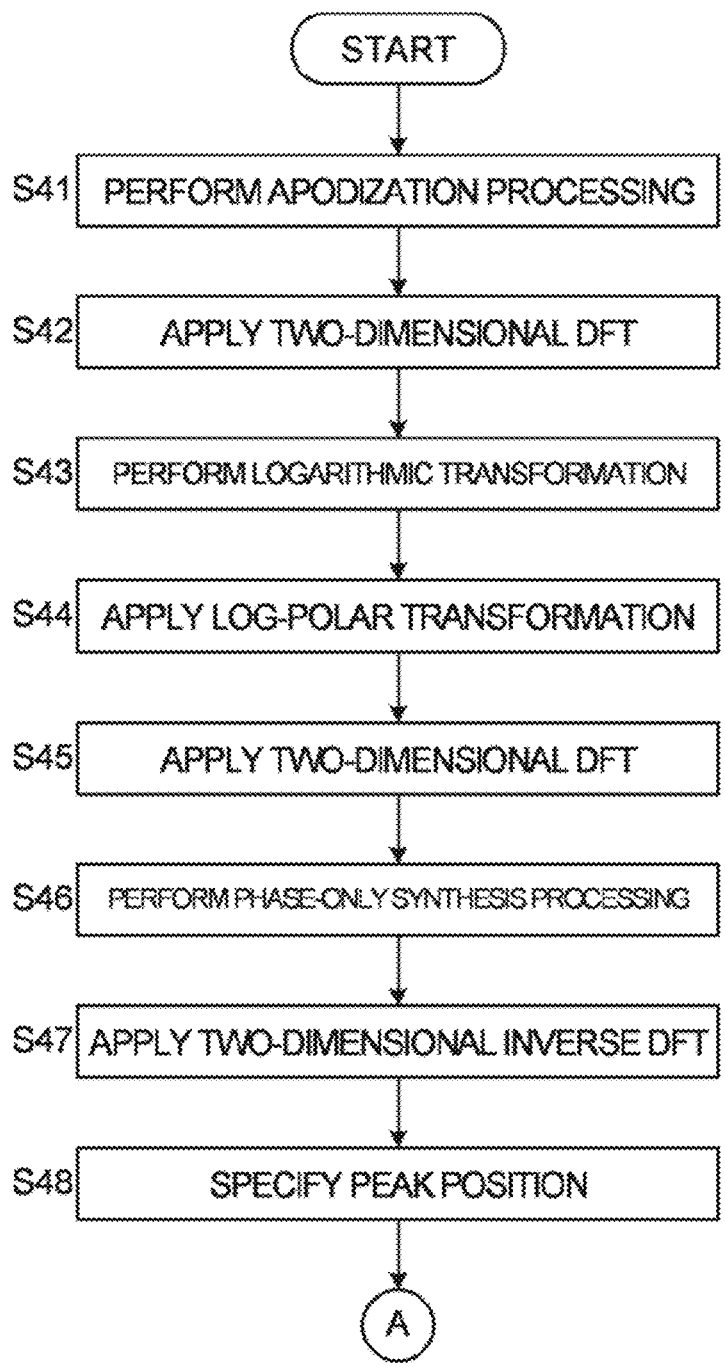
FIG. 11 is a flow chart of an operation example of the ophthalmologic apparatus according to the embodiments.
Figure 12:
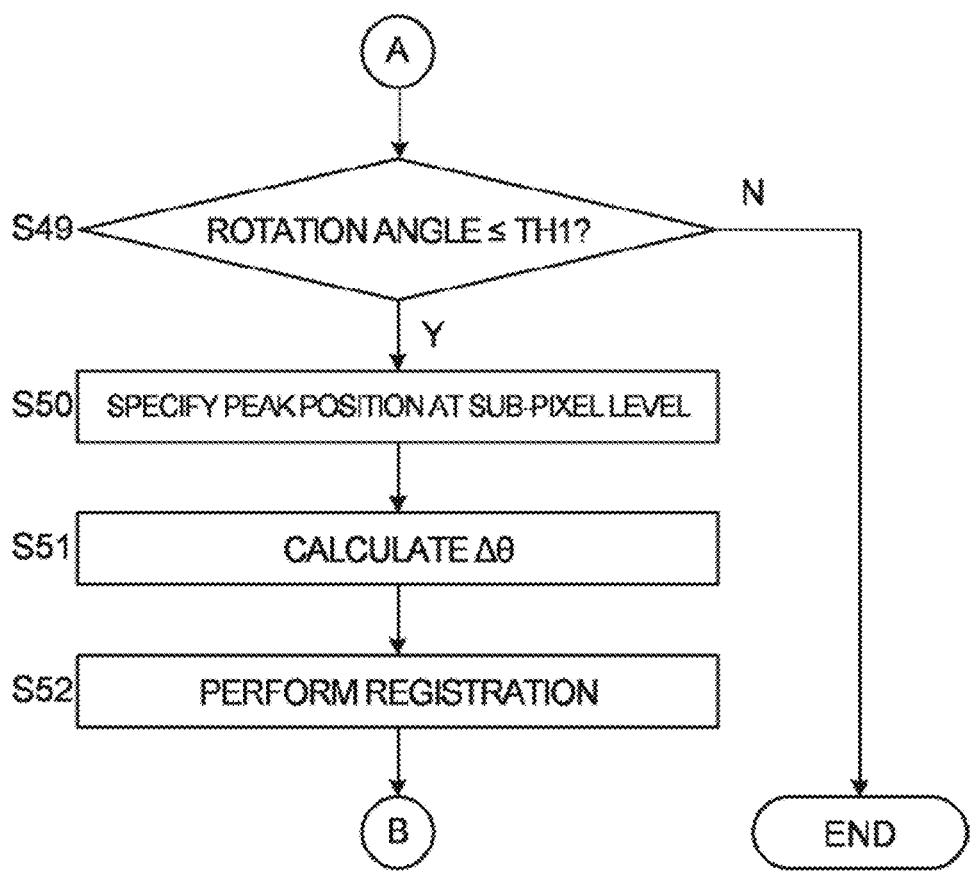
FIG. 12 is a flow chart of an operation example of the ophthalmologic apparatus according to the embodiments.
Figure 13:
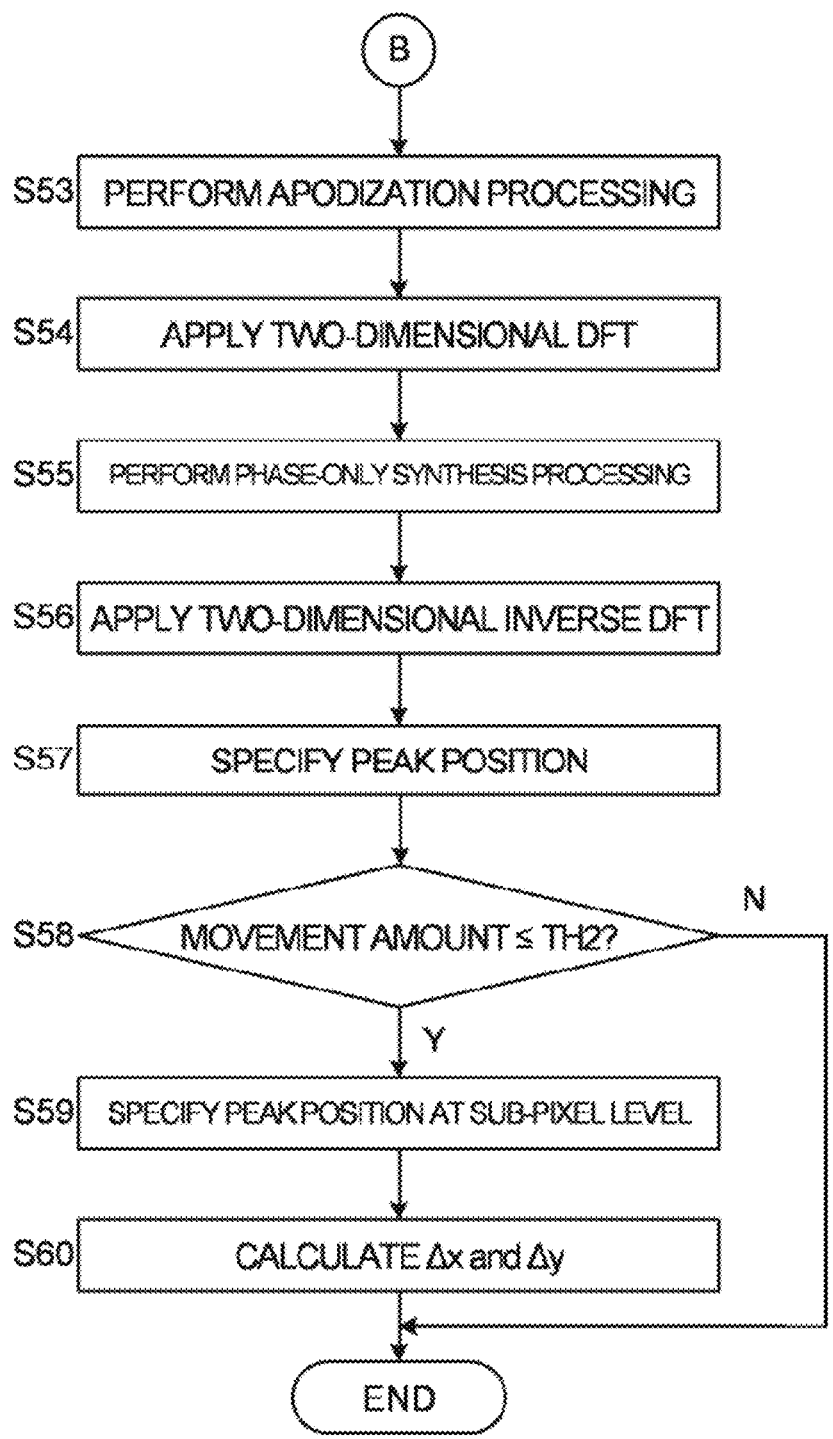
FIG. 13 is a flow chart of an operation example of the ophthalmologic apparatus according to the embodiments.

FIGS. 11 to 13 illustrate an example of a flow of the target image processing according to the embodiments. The target image processing includes a processing of generating target POC data for the target image, a processing of calculating a rotational movement amount and a rotational movement direction, a registration processing, and a processing of calculating a parallel movement amount and a parallel movement direction.

(S41: Perform Apodization Processing)

First, the rotational movement amount calculator 241 performs an apodization processing on the partial image. This processing is performed in the same manner as described for step S21. The apodization processing is performed by, for example, an apodization processor (not illustrated) in the first transformation processor 301 or the rotational movement amount calculator 241.

(S42: Apply Two-Dimensional DFT)

Next, the first transformation processor 301 applies a two-dimensional DFT to the result of the apodization processing performed on the partial image in step S S41.

(S43: Perform Logarithmic Transformation)

Next, the logarithmic transformation unit 302 applies a logarithmic transformation to the processing result of the two-dimensional DFT in step S24. This logarithmic transformation be performed in the same way as in step S23.

(S44: Apply Log-Polar Transformation)

Next, the polar coordinate transformation unit 303 applies a Log-Polar transformation to the processing result of the logarithmic transformation in step S43. The apodization processing is performed in the same manner as described for step S24.

(S45: Apply Two-Dimensional DFT)

Next, the second transformation processor 304 applies a two-dimensional DFT to the processing result of the Log-Polar transformation in step S44.

(S46: Perform Phase only Synthesis Processing)

Next, the first phase-only synthesis unit 305 performs the phase only synthesis processing according to Equation (3) using the first base POC data stored in the storage unit 212 in step S26 and the target POC data obtained by normalizing the processing result of the two-dimensional DFT in step S45 with the amplitude component. Here, the first base POC data is the base POC data generated for the partial image.

(S47: Apply Two-Dimensional IDFT)

Thereafter, the first inverse transformation processor 306 applies a two-dimensional IDFT to the processing result of the phase only synthesis processing according to Equation (4).

(S48: Specify Peak Position)

By specifying a peak position from the processing result of step S47, the radius vector (a coordinate in the x direction) and the argument (a coordinate in the y direction) with a high correlation value are specified at the pixel level. Accordingly, the rotational movement amount calculator 241 obtains the peak value of the processing result in step S47, obtains the address of a peak position corresponding to the peak value, and stores it in the storage unit 212.

(S49: Rotation Angle≤TH1?)

The rotational movement amount calculator 241 determines whether or not the rotation angle (absolute value) corresponding to the argument is equal to or less than the first threshold value TH1 based on the address of the peak position stored in the storage unit 212. Having determined that the rotation angle is not equal to or less than the first threshold value TH1 (S49: N), the rotational movement amount calculator 241 determines it as an error, and ends a series of processes (END). Meanwhile, having determined that the rotation angle is equal to or less than the first threshold value TH1 (S49: Y), the processing performed by the rotational movement amount calculator 241 moves to step S50.

(S50: Specify Peak Position at Sub-Pixel Level)

When it is determined that the rotation angle is equal to or less than the first threshold value TH1 (S49: Y), the rotational movement amount calculator 241 calculates a correlation value of the phase only correlation function at the sub-pixel level according to Equation (7). In particular, as disclosed in Japanese Unexamined Patent Application Publication No. 2015-043898, the rotational movement amount calculator 241 obtains a plurality of values of the phase only correlation function at the sub-pixel level represented by Equation (7) and specifies the argument (the coordinate of the y direction) with a high correlation value by specifying a peak position. The rotational movement amount calculator 241 obtains the address corresponding to the specified peak value and stores it in the storage unit 212.

(S51: Calculate $\Delta\theta$)

Next, as disclosed in Japanese Unexamined Patent Application Publication No. 2015-043898, the rotational movement amount calculator 241 calculates a rotational movement amount $\Delta\theta$ corresponding to the peak position specified at the sub-pixel level. The rotational movement direction is specified by the sign of $\Delta\theta$.

(S52: Perform Registration)

When the rotational movement amount $\Delta\theta$ is calculated, the registration unit 242 rotates the target image stored in the storage unit 212 by $-\Delta\theta$.

(S53: Perform Apodization Processing)

Subsequently, the parallel movement amount calculator 243 calculates a parallel movement amount and a parallel movement direction. Specifically, the parallel movement amount calculator 243 performs the apodization processing on the partial image registered in step S52. This processing is performed by an apodization processor (not illustrated) in the third transformation processor 311 or the parallel movement amount calculator 243.

(S54: Apply Two-Dimensional DFT)

Next, the third transformation processor 311 applies a two-dimensional DFT to the result of the apodization processing performed on the partial image in step S53.

(S55: Perform Phase only Synthesis Processing)

Next, the second phase-only synthesis unit 312 performs the phase only synthesis processing according to Equation (3) using the second base POC data stored in the storage unit 212 in step S29 and the target POC data obtained by normalizing the processing result of the two-dimensional DFT in step S54 with the amplitude component.

(S56: Apply Two-Dimensional IDFT)

Thereafter, the second inverse transformation processor 313 applies a two-dimensional IDFT to the processing result of the phase only synthesis processing according to Equation (4).

(S57: Specify Peak Position)

By specifying a peak position from the processing result of step S59, the coordinate in the x direction and the coordinate in the y direction corresponding to the correlation value are specified. The parallel movement amount calculator 243 obtains the peak value of the processing result in step S59, obtains the address of a peak position corresponding to the peak value, and stores it in the storage unit 212.

(S58: Movement Amount≤TH2?)

The parallel movement amount calculator 243 determines whether, for example, the movement amount (absolute value) in the x direction and the movement amount (absolute value) in the y direction are equal to or less than the second threshold value TH2 based on the address of the peak position stored in the storage unit 212. Having determined that the movement amount in the x direction and the movement amount in the y direction are not equal to or less than the second threshold value TH2 (S58: N), the parallel movement amount calculator 243 determines it as an error, and ends a series of processes (END). Meanwhile, having determined that the movement amount in the x direction and the movement amount in the y direction are not equal to or less than the second threshold value TH2 (S58: Y), the processing performed by the parallel movement amount calculator 243 moves to step S59.

(S59: Specify Peak Position at Sub-Pixel Level)

When it is determined that the movement amount in the x direction and the movement amount in the y direction are not equal to or less than the second threshold value TH2 (S58: Y), the parallel movement amount calculator 243 calculates a correlation value of the phase only correlation function at the sub-pixel level according to Equation (7). In particular, as disclosed in Japanese Unexamined Patent Application Publication No. 2015-043898, the parallel movement amount calculator 243 obtains a plurality of values of the phase only correlation function at the sub-pixel level represented by Equation (7) and specifies the movement amount (the coordinate of the x direction and the coordinate of the y direction) with a high correlation value by specifying a peak position. The parallel movement amount calculator 243 obtains the address corresponding to the specified peak value and stores it in the storage unit 212.

(S60: Calculate $\Delta x$, $\Delta y$)

Next, as disclosed in Japanese Unexamined Patent Application Publication No. 2015-043898, the parallel movement amount calculator 243 calculates the parallel movement amounts $\Delta x$ and $\Delta y$ corresponding to the peak position specified at the sub-pixel level. The parallel movement direction is specified by the sing of $\Delta x$ and $\Delta y$. With this, a series of processes of the target image processing is completed (END).

The rotational movement amount $\Delta \theta$, the rotational movement direction, the parallel movement amounts $\Delta x$ and $\Delta y$, and the parallel movement direction calculated as above is output to the controller 210. The controller 210 (the main controller 211) controls the optical system driver 1A based on the calculated parallel movement amounts $\Delta x$ and $\Delta y$ to move the optical system provided in the apparatus three-dimensionally, thereby performing tracking. The controller 210 may control the optical system driver 1A based on the rotational movement amount $\Delta \theta$ and the rotational movement direction.

[Effects]

The ophthalmologic apparatus and the method of controlling the ophthalmologic apparatus according to the embodiments is explained.

An ophthalmologic apparatus (1) according to the embodiments comprises an optical system (optical system shown in FIG. 1, interference optical system included in the imaging optical system 30 or the OCT unit 100), an image acquiring unit (CCD image sensor 35), a rotational movement amount calculator (241), a registration unit (242), a parallel movement amount calculator (243), a movement mechanism (optical system driver 1A), and a controller (210, main controller 211). The optical system is used for acquiring data of a subject's eye (E) optically. The image acquiring unit acquires a first image (base image) of an anterior segment of the subject's eye and a second image (target image) of the anterior segment at different timings from each other. The rotational movement amount calculator calculates a rotational movement amount between a partial image in the second image and a corresponding partial image in the first image, the corresponding partial image corresponding to the partial image. The registration unit performs registration between the corresponding partial image and the partial image in a rotation direction based on the rotational movement amount. The parallel movement amount calculator performs a phase only correlation processing on the corresponding partial image and the partial image registered by the registration unit to calculate a parallel movement amount between the corresponding partial image and the partial image. The movement mechanism moves the subject's eye and the optical system relative to each other. The controller controls the movement mechanism based on at least one of the rotational movement amount and the parallel movement amount.

In such a configuration, registration between the partial image in the second image of the anterior segment of the subject's eye and the corresponding partial image corresponding to the partial image in the first image in the rotation direction, the first image and the second image being acquired at different timings, is performed. And then, the phase only correlation processing on the corresponding partial image and the partial image registered is performed. thereby, the ophthalmologic apparatus capable of calculating the parallel movement amount, etc. between the corresponding partial image and the partial image and moving the subject's eye and the optical system relative to each other can be provided. Thereby, the ophthalmologic apparatus capable of performing tracking with high precision in case of measuring or imaging the anterior segment of the subject's eye can be provided.

Further, the ophthalmologic apparatus according to the embodiments further may comprise a specifying unit (analyzer 231) that specifies the partial image in the second image. The rotational movement calculator may calculate the rotational movement amount between the corresponding partial image and the partial image specified by the specifying unit.

According to such a configuration, the ophthalmologic apparatus capable of perform tracking with high precision using the partial image specified by the specifying unit and the corresponding partial image corresponding to the partial image in the first image can be provided.

Further, in the ophthalmologic apparatus according to the embodiments, the specifying unit may specify the partial image based on the first image and the second image.

According to such a configuration, the partial image suitable for applying the phase only correlation processing can be specified, since the partial image can be specified from the difference between the first image and the second image, etc. Thereby, a minute misregistration amount can be obtained by using the phase only correlation processing and tracking with higher precision can be performed.

Further, in the ophthalmologic apparatus according to the embodiments, the specifying unit may specify, as the partial image, an image of a region of which movement amount with respect the first image is equal to or larger than a first threshold value in the second image.

According to such a configuration, even if both of the first image and the second image include a region which do not move, a minute misregistration amount can be obtained by using the phase only correlation processing and tracking with higher precision can be performed, since an image of a region which moves with respect to the first image is specified as the partial image.

Further, in the ophthalmologic apparatus according to the embodiments, the specifying unit may specify a region of which movement amount with respect the first image is equal to or less than a second threshold value in the second image, and specify, as the partial image, an image of a region other than the specified region in the second image.

According to such a configuration, even if both of the first image and the second image include a region which do not move, a minute misregistration amount can be obtained by using the phase only correlation processing and tracking with higher precision can be performed, since an image excluding a region which do not move with respect to the first image is specified as the partial image.

Further, in the ophthalmologic apparatus according to the embodiments, the specifying unit may specify an image of a region in which an eyelid or an eyelash is represented in the second image, and specify, as the partial image, an image of a region other than the specified region in the second image.

According to such a configuration, even if the eyelid or the eyelash is represented in the first image and the second image, a minute misregistration amount can be obtained by using the phase only correlation processing and tracking with higher precision can be performed, since an image of region where the eyelid or the eyelash is not represented in the second image is specified as the partial image.

Further, in the ophthalmologic apparatus according to the embodiments, the specifying unit may specify, as the partial image, an image of a predetermined region in the second image.

According to such a configuration, even if both of the first image and the second image include a region which do not move, a minute misregistration amount can be obtained by using the phase only correlation processing and tracking with higher precision can be performed, since an image of a region cut out from the second image so that the angle of view becomes narrow is specified as the partial image.

Further, in the ophthalmologic apparatus according to the embodiments, the predetermined region may include a region corresponding to a pupil of the subject's eye, and may be a region where upper eyelid, lower eyelid, and an eyelash of the subject's eye are not represented.

According to such a configuration, even if both of the first image and the second image include a region which do not move, a minute misregistration amount can be obtained by using the phase only correlation processing and tracking with higher precision can be performed, since an image of a region where the region corresponding to the pupil is represented and the upper eyelid, the lower eyelid, and the eyelash are not represented is specified as the partial image.

Further, in the ophthalmologic apparatus according to the embodiments, the rotational movement amount calculator may perform the phase only correlation processing on the corresponding partial image and the partial image to calculate the rotational movement amount.

According to such a configuration, the registration between the corresponding partial image and the partial image can be performed based on the rotational movement amount calculated with high precision (for example, at the sub-pixel level). Thereby, the more minute displacement amount (misregistration amount) can be obtained and the tracking can be performed with higher precision.

Further, a method of controlling an ophthalmologic apparatus (1) according to the embodiments is a method of controlling an ophthalmologic apparatus comprising an optical system (optical system shown in FIG. 1, interference optical system included in the imaging optical system 30 or the OCT unit 100) for acquiring data of a subject's eye optically, an image acquiring unit (CCD image sensor 35) that acquires a first image (base image) of an anterior segment of the subject's eye and a second image (target image) of the anterior segment at different timings from each other, and a movement mechanism (optical driver 1A) that moves the subject's eye and the optical system relative to each other. The method of the ophthalmologic apparatus comprises a rotational movement amount calculating step of calculating a rotational movement amount between a partial image in the second image and a corresponding partial image in the first image, the corresponding partial image corresponding to the partial image, a registration step of performing registration between the corresponding partial image and the partial image in a rotation direction based on the rotational movement amount, a parallel movement amount calculating step of performing a phase only correlation processing on the corresponding partial image and the partial image registered in the registration step to calculate a parallel movement amount between the corresponding partial image and the partial image, and a control step of controlling the movement mechanism based on at least one of the rotational movement amount and the parallel movement amount.

In such a configuration, registration between the partial image in the second image of the anterior segment of the subject's eye and the corresponding partial image corresponding to the partial image in the first image in the rotation direction, the first image and the second image being acquired at different timings, is performed. And then, the subject's eye and the optical system can be moved relative to each other by performing the phase only correlation processing on the corresponding partial image and the partial image registered and then calculating the parallel movement amount, etc. between the corresponding partial image and the partial image. Thereby, tracking with high precision can be performed in case of measuring or imaging the anterior segment of the subject's eye.

Further, the method of controlling the ophthalmologic apparatus according to the embodiments further may comprise a specifying step of specifying the partial image in the second image. The rotational movement amount calculating step may comprise calculating the rotational movement amount between the corresponding partial image and the partial image specified in the specifying step.

According to such a configuration, tracking with high precision can be performed by using the partial image specified in the specifying step and the corresponding partial image corresponding to the partial image in the first image.

Further, in the method of controlling the ophthalmologic apparatus according to the embodiments, the specifying step may comprise specifying an image of a region of which movement amount with respect the first image is equal to or larger than a first threshold value in the second image, as the partial image.

According to such a configuration, even if both of the first image and the second image include a region which do not move, a minute misregistration amount can be obtained by using the phase only correlation processing and tracking with higher precision can be performed, since an image of a region which moves with respect to the first image is specified as the partial image.

Further, in the method of controlling the ophthalmologic apparatus according to the embodiments, the specifying step may comprise specifying a region of which movement amount with respect the first image is equal to or less than a second threshold value in the second image, and specifying an image of a region other than the specified region in the second image as the partial image.

According to such a configuration, even if both of the first image and the second image include a region which do not move, a minute misregistration amount can be obtained by using the phase only correlation processing and tracking with higher precision can be performed, since an image excluding a region which do not move with respect to the first image is specified as the partial image.

Further, in the method of controlling the ophthalmologic apparatus according to the embodiments, the specifying step may comprise specifying a predetermined region in the second image as the partial image.

According to such a configuration, even if both of the first image and the second image include a region which do not move, a minute misregistration amount can be obtained by using the phase only correlation processing and tracking with higher precision can be performed, since an image of a region cut out from the second image so that the angle of view becomes narrow is specified as the partial image.

Examples of Modifications

The above-described embodiments are merely examples for carrying out the present invention. Those who intend to implement the present invention can apply any modification, omission, addition, or the like within the scope of the gist of the present invention.

In the above embodiments, examples are described in which the configuration of the optical system has the configuration shown in FIG. 1; however, they are not so limited. The optical system according to the embodiments may include an optical system to project a laser light beam on a treatment site in the fundus, an optical system to move a visual target in a state where the subject's eye is being fixated.

The ophthalmologic apparatus may include two or more anterior segment cameras for photographing the anterior segment of the subject's eye E from different directions. In this case, the controller according to the embodiments can perform the alignment in the z direction from a parallax obtained based on the two or more photographed images of the anterior segment from different directions each other acquired by using these cameras.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
an optical system for acquiring data of a subject's eye optically;
an image sensor that acquires a first image of an anterior segment of the subject's eye and a second image of the anterior segment at different timings from each other;
processing circuitry configured to calculate a rotational movement amount between a partial image in the second image and a corresponding partial image in the first image, the corresponding partial image corresponding to the partial image;
the processing circuitry further configured to calculate a misregistration between the corresponding partial image and the partial image in a rotation direction based on the rotational movement amount;
the processing circuitry further configured to perform a phase only correlation processing only on the corresponding partial image and the partial image based on the calculated misregistration to calculate a parallel movement amount between the corresponding partial image and the partial image;
an actuator that moves the subject's eye and the optical system relative to each other;
the processing circuitry further configured to control the actuator based on at least one of the rotational movement amount and the parallel movement amount;
the processing circuitry further configured to specify the partial image in the second image based on a difference between the first image and the second image; and
the processing circuitry calculates the rotational movement amount between the corresponding partial image and the specified partial image.

2. The ophthalmologic apparatus of claim 1, wherein the processing circuitry is further configured to specify, as the partial image, an image of a region of in the second image for which a movement amount with respect the first image is equal to or larger than a first threshold value.

3. The ophthalmologic apparatus of claim 1, wherein
the processing circuitry is further configured to specify, as the partial image, an image of a predetermined region in the second image.

4. The ophthalmologic apparatus of claim 3, wherein
the predetermined region includes a region corresponding to a pupil of the subject's eye, and is a region where upper eyelid, lower eyelid, and an eyelash of the subject's eye are not represented.

5. The ophthalmologic apparatus of claim 1, wherein
the processing circuitry is further configured to perform the phase only correlation processing on the corresponding partial image and the partial image to calculate the rotational movement amount.

6. A method of controlling an ophthalmologic apparatus, the method comprising:
acquiring data of a subject's eye optically;
acquiring, using an image sensor, a first image of an anterior segment of the subject's eye and a second image of the anterior segment at different timings from each other;
moving the subject's eye and the optical system relative to each other using an actuator,
calculating a rotational movement amount between a partial image in the second image and a corresponding partial image in the first image, the corresponding partial image corresponding to the partial image;
calculating a misregistration between the corresponding partial image and the partial image in a rotation direction based on the rotational movement amount;
performing a phase only correlation processing only on the corresponding partial image and the partial image based on the calculated misregistration to calculate a parallel movement amount between the corresponding partial image and the partial image;
controlling the actuator based on at least one of the rotational movement amount and the parallel movement amount;
specifying the partial image as a region of the second image for which a movement amount with respect to the first image is equal to or larger than a first threshold value; and
the calculating further includes calculating the rotational movement amount between the corresponding partial image and the specified partial image.

* * * * *